Figure 1:
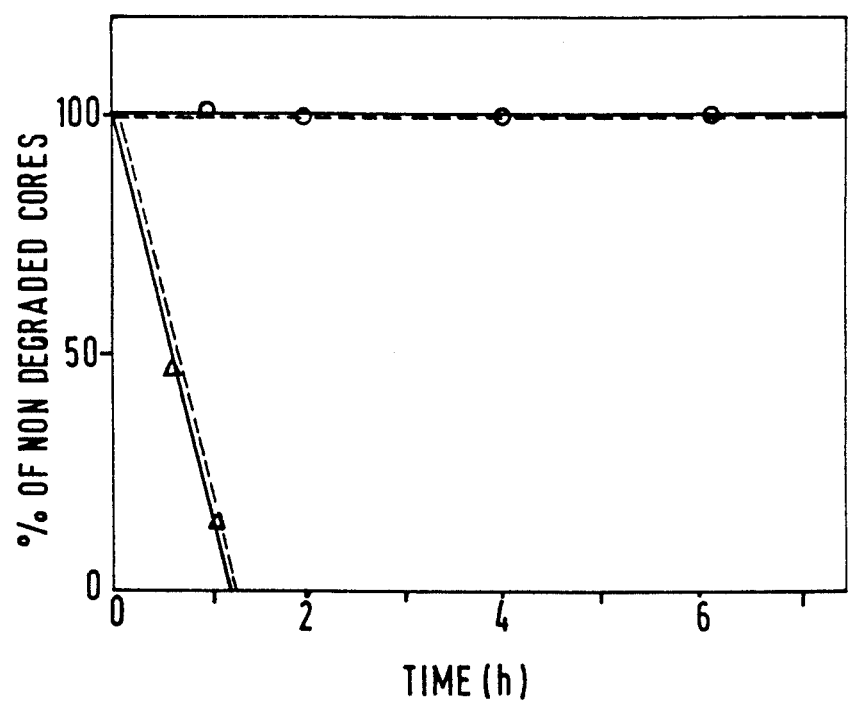

United States Patent [19]

Lebleu et al.

[11] Patent Number: 4,981,957

[45] Date of Patent: Jan. 1, 1991

[54] OLIGONUCLEOTIDES WITH MODIFIED PHOSPHATE AND MODIFIED CARBOHYDRATE MOIETIES AT THE RESPECTIVE CHAIN TERMINI

[75] Inventors: Bernard Lebleu, Montpellier; Bernard Bayard, Castelnau Le Lez, both of France

[73] Assignee: Centre National De La Recherche Scientifique, Paris, France

[21] Appl. No.: 756,369

[22] Filed: Jul. 18, 1985

[30] Foreign Application Priority Data

Jul. 19, 1984 [FR] France ................ 84 11469

[51] Int. Cl.$^5$ ................................ C07H 21/02
[52] U.S. Cl. ........................ 536/27; 536/28; 536/29
[58] Field of Search .............. 514/46, 47; 536/27, 536/28, 29

[56] References Cited

U.S. PATENT DOCUMENTS

| 4,378,352 | 3/1983 | Kimchi et al. | 536/27 |
| 4,515,781 | 5/1985 | Torrence et al. | 514/46 |

FOREIGN PATENT DOCUMENTS

| 0142296 | 11/1981 | Japan | 536/27 |
| 0049399 | 3/1983 | Japan | 536/28 |
| 0950733 | 8/1982 | U.S.S.R. | 536/24 |

OTHER PUBLICATIONS

Baglioni et al, *The Journal of Biological Chemistry*, vol. 256, No. 7, pp. 3253-3257 (Apr. 10, 1981).
Gosselin et al., *Tetrahedron Letters*, vol. 22, No. 47, pp. 4699-4702 (1981).
Haugh et al, *Eur. J. Biochem.*, vol. 132, pp. 77-84 (1983).
Torrence et al, *J. Med. Chem.*, vol. 26, No. 12, pp. 1674-1678 (Dec. 1983).
Hughes et al, *Biochemistry*, vol. 22, No. 9, pp. 2127-2135 (1983).
Kariko et al, *Chem. Abstr.*, 103, 16829h, 1985.
Knight et al., *Methods in Enzymology*, vol. 79, pt. A., pp. 216-227, 1981.
Eppstein et al., *Nature*, vol. 302, pp. 723-724, 1983.
Justesen et al., *Proc. Nat. Acad Sci (Biochem).*, vol. 77, pp. 4618-4622, 1980.
March, Advanced Organic Chemistry, McGraw-Hill Book Co., 1968, New York, pp. 306 (Acetal Hydrolysis) & 678 ($BH_4^\ominus$ + Aldehydes).

*Primary Examiner*—Ronald W. Griffin
*Assistant Examiner*—L. Eric Crane
*Attorney, Agent, or Firm*—Fleit, Jacobson, Cohn, Price, Holman & Stern

[57] ABSTRACT

The invention relates to novel oligonucleotides, the process for their preparation and their biological uses as mediators of the action of interferon. The oligonucleotides according to the invention have the formula:

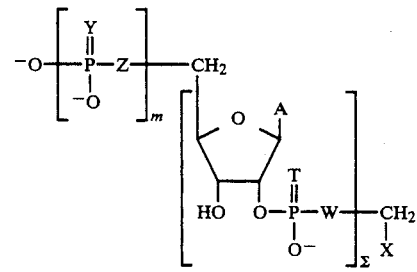

in which Y and T are identical or different and represent particularly O, S, Z and W are identical or different and represent particularly O, S, one at least of the elements Y and Z being different from oxygen, X represents particularly —$CHOHCH_2OH$, $\Sigma$ is a whole number equal to or greater than 2, A represents adenine or one of its derivatives. These oligonucleotides have antiviral use.

13 Claims, 2 Drawing Sheets

OLIGONUCLEOTIDES WITH MODIFIED PHOSPHATE AND MODIFIED CARBOHYDRATE MOIETIES AT THE RESPECTIVE CHAIN TERMINI

BACKGROUND OF THE INVENTION

The invention relates to novel oligonucleotides, the process for their preparation and their biological use as mediators in the development of the action of interferons, particularly in the development of a part at least of the antiviral action of interferons.

It is known that interferons constitute a family of proteins characterised particularly by their antiviral properties.

It has been observed that the antiviral effect of interferons is mediated by the synthesis of particular proteins. Specific tests have enabled the function of two of them to be identified, which are both enzymes (BAGLIONI. C., 1979, Interferon induced enzymatic activities and their role in the antiviral state. Cell 17, 255-264).

One of them is a polymerase oligonucleotide (2-5A synthetase). This polymerase oligonucleotide catalyses, after activation by bicatenary RNAs and from ATP, the synthesis of a family of oligonucleotides.

These oligonucleotides are short chains of adenosines connected by phosphodiester linkages 2'→5' (KERR I. M. et BROWN R. E., 1978, pppA2'-p5'A2'p5'A: An inhibitor of protein synthesis synthesized with an enzyme fraction from interferon treated cells. PNAS 75, 256-260) of which the general formula may be represented by pppA (2' p5'A)$_n$. These oligonucleotides may be denoted by "oligonucleotides 2'-5'" particularly "oligoadenylates 2'-5'" or by (2'-5') (A)$_n$. One of these oligoadenylates may be represented by the following formula:

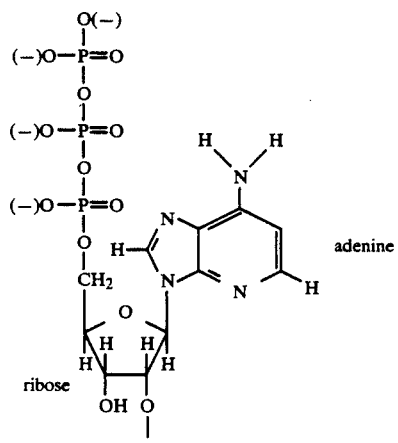

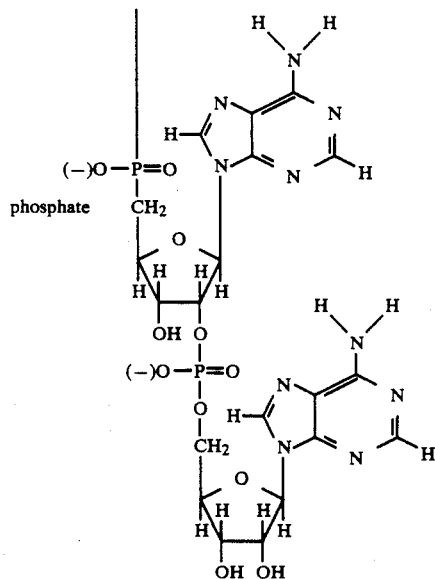

It is composed of short chains containing several adenosine groups (adenine+ribose) joined to one another through phosphodiester linkages, as shown, and in which the position at 5' of the adenine nucleus of the terminal adenosine is linked to a variable number of phosphate groups (up to 3 on the 2'→5' oligoadenylate shown).

When the oligoadenylate 2'→5' is totally desphosphorylated, that is to say when the position at 5' of the adenine nucleus of the terminal adenosine is free from the abovesaid variable number of phosphate groups, the resulting compound is denoted by "nucleus(2'→5-')A3'," which is an abbreviation for "riboadenylyl (2'→5') riboadenylyl (2'→5') riboadenosine".

The 2'-5' nuclei corresponding to the dephosphorylated (2'-5') oligoadenylates are also called "cores".

In the rest of the description, the 2'-5' oligoadenylates induced in the treated cells by interferon will also be denoted by "unmodified 2'-5' oligoadenylate".

It is accepted that the expression "oligoadenylates 2'→5'" mentioned above and used below will denote also, for convenience of language, the nucleus (2'-5') (A)$_n$ partly or entirely dephosphorylated.

The discovery of these 2'→5' oligoadenylates has revealed a novel class of biologically active oligonucleotides, which are assumed to show an important role as mediators of the action of interferon, particularly in the activation of L. endoribionuclease, which is present both in the cells treated by interferon and in those untreated, and in the inhibition of the synthesis of proteins. However the phosphodiester 2'→5' linkages of these adenylates are rapidly cleaved by an enzyme denoted by 2'-phosphodiesterase (cf. the BAGLIONI reference mentioned above).

L endoribonuclease as well as 2-phosphodiesterase are present at levels substantially equal in the treated cells as well as in the cells untreated with interferon.

When the cell is treated with interferon, the concentration of oligonucleotide 2'-5' polymerase increases. Infection by certain viruses of cells so treated results in the production at the viral replication site of NRA bicatenaries activating oligonucleotide 2'-5' polymerase.

There results an increase, transitory and possibly localised, at the replication site of the virus, of the concentration of oligoadenylate 2'→5' (Nilsen T. W. et Baglioni C., 1984. Interferon 5, J. Gresser Ed., Academic Press, New York). These oligonucleotides activate themselves by specifically binding therein endoribonuclease L which degrades the viral RNA messengers.

When the interferon is removed from the culture medium, the activity of the oligonucleotide 2'-5' polymerase decreases and the cell loses its antiviral state.

The synthesis of the proteins induced by interferon is transient and, consequently, the cells kept in the tissue cultures do not maintain a high level of these proteins.

In addition, the 2'→5' oligoadenylates induced in the cells treated with interferon exhibit the drawback of having a low metabolic stability. In fact, the unmodified 2'→5' oligoadenylates are, on the one hand, rapidly hydrolysed by a specific phosphodiesterase degrading the molecule progressively from its ribose 2' terminal, on the other hand, are degraded under the action of a phosphatase on the side of the first ribose connected with the variable number of phosphate groups. (Lebleu B. et Content J., 1982, Interferon 3, J. Gresser Ed. Academic Press, New York).

Researches have been undertaken to find similar compounds to the unmodified 2'→5' oligoadenylates and having increased activity, in comparison with the 2'→5' oligoadenylates induced in cells treated with interferon (BAGLIONI C. et coll., 1981, Analogs of (2'-5')oligo(A). Endonuclease activation and inhibition of protein synthesis in intact cells. The Journal of Biological Chemistry, vol. 256, n° 7, p. 3, 253-3 257).

Various researches have been carried out to synthesise (enzymatically and/or chemically) modified analogs of 2'→5' oligoadenylates induced in cells treated with interferon, which would be resistant to the degradation actions, without losing their biological activity.

Among these researches, it is possible to cite enzymatic synthesis by means of 2'→5A synthetase of "cordycepine 2→5A" from 2' deoxyadenosine triphosphate (DOETSCH et coll., 1981).

Cordycepine has been considered as inhibiting the synthesis of the proteins in an acellular system and the corresponding dephosphorylated compound ("core" or "nucleus") has been considered as blocking the blastic transformation of human lymphocytes.

The results have however been disputed (CHAPEKAR M. S. et coll., 1983, Biochem. Res. Comm., 115, 137-143) and it seems that the effects observed have been caused by the accumulation of toxic degradation products of cordycepine.

It is also possible to cite, among the researches carried out, the chemical synthesis of an analog of the nucleus of 2'→5' oligoadenylates, in a xylose series (IMBACH J. L. et coll., 1981, Tetrahedron Letters, vol. 22. n° 47, p. 4 699-4 702), named "xylo 2'-5'A". This analog is shown to present greater stability with respect to phosphodiesterases than the nucleus of unmodified 2'-5' oligoadenylates, an interesting activity with respect to a DNA virus, such as Herpes, but not with respect to RNA virus (EPPSTEIN D., et coll., 1983, Nature, 302, 723-724).

There can also be mentioned the chemical synthesis and the modification at its 2' terminal end of a 2'-5' oligoadenylate into a compound called "tailed 2'-5' A" in which a hexylamine chain has been associated with a morpholine nucleus, itself condensed by a phosphate group onto the OH group at the 2' position of the terminal ribose. This derivative is very stable with respect to phosphodiesterases and activates L endoribonuclease in an acellular system (IMAI J. et coll., 1982. J. Biochem. Chem., 257, 12 739-12 741), but its antiviral activity has not been established.

Among these researches, it is possible also to mention the chemical synthesis of modified derivatives of 2'-5' oligoadenylates such as the derivatives of 2'-5'A triphosphates (represented by the formula pppA2'p5'A2'-p5A) in which the phosphorus atoms at the beta and gamma positions of the triphosphate group at the 5' position are separated by a methylene group.

Another modification to obtain modified 2'-5'A oligoadenylates relates to the replacement of a hydroxyl group at the 3' position by an $OCH_3$ group either in the terminal adenosine, or in all the adenosines (J. A. J. DEN HARTOG et coll., 1981, J. Org. Chem., 46, 2 242-2 251).

However it is shown that these two latter groups of compounds were weakly active, even inactive and did not show satisfactory metabolic stability (cf. the reference mentioned above and BAGLIONI et coll., 1981, J. Biol. Chem., 256, 2 353-2 357).

Other analogs, such as 5'S-methylthiophosphorothioates have been synthesised. Certain of these analogs are revealed to be stable. But a priori, the apparent differences of properties of these analogs does not seem to permit their use on human cells for therapeutic purposes to be envisaged (HAUGH M. C., CAYLEY P. J. et coll., 1983, Europ. J. Biochem., 132, 77-84).

Investigations have also borne on the incidence of the modification of the one or more phosphate groups carried by the carbon at the 5' position of 2'-5' oligoadenylates with respect to antimitogenic activity (cf. TORRENCE et coll., 1983, J. Medicinal Chemistry 26, n° 12, 1674-1678). The compounds prepared within the scope of these researches are shown to present antimitogenic activity, but it has been found that certain of them do not activate endoribonuclease L in an in vitro cellular system, which prevents the establishment of a correlation between antimitogenic activity and antiviral action.

Other similar oligonucleotides of (2'-5') $(A)_m$ have been synthesised enzymatically by replacing the adenosine, particularly by 8-azaadenosine, toyocamycine, sangivamycine, formycine, 8-bromoadenosine, tubercidine and guanosine. It was shown that the majority of these compounds were degraded in cellular extracts. Only inhibition tests of the synthesis of proteins and of cellular proliferation have been carried out in intact cells, but the antiviral activity has not been established (B. G. HUGHES and R. K. ROBINS, 1983, Biochemistry, 22, n°9, 2 127-2 135). None of the analogs of (2'-5')(A) synthesized hitherto have shown stability properties -both with respect to phosphodiesterases and phosphases-, and sufficient biological activity to be able to envisage using them in the therapeutic treatment of viral infections.

GENERAL DESCRIPTION OF THE INVENTION

Applicants have discovered new oligonucleotides having a structure different from that of unmodified 2'-5'A oligoadenylates and its known analogs, having an antiviral activity similar to that of interferon, which are resistant with respect to degradation by 2'-phosphodiesterase and by phosphatases permitting their use in the treatment of viral infections to be contemplated, in so far as they are associated with appropriate carriers enabling them to cross the cell membrans.

One of the aspects of the invention is to propose new oligonucleotides which can be recognized by L endoribonuclease, that is to say which can form with L endoribonuclease an active complex.

Another aspect of the invention is to provide new oligonucleotides which have an increased resistance with respect to degradation by 2'-phosphodiesterase.

Another aspect of the invention is to provide new oligonucleotides which have an increased resistance relative to phosphatases.

Another aspect of the invention is to provide new biologically active oligonucleotides, which show particularly an effective antiviral activity, in so far as they are associated with appropriate carriers enabling them to cross the cell membrans.

Another aspect of the invention is to provide new oligonucleotides liable to be used in the preparation of biologically active compounds, which present particularly an efficient antiviral activity.

These various aspects are achieved by novel oligonucleotides comprising a chain containing n nucleoside units, identical or different, n being equal to or higher than 2, these nucleoside units being joined by 2'-5' linkages, which comprise a group of linkages containing at least one phosphorus atom and in which:

The nucleosidic "first unit" of the above-said chain is linked through its carbon at the 5' position to a variable number of phosphate groups, and one of the oxygen atoms of at least one of the phosphate groups, which oxygen atom joined only to the phosphorus of the phosphate groups and not taking part in the linkage between two phosphate groups, is replaced by an atom of sulfur, of selenium or an NH group, and/or one at least of the linkages between two adjacent phosphate groups comprises an NH group or a sulfur atom; and/or the nucleosidic "last unit" of the above-said chain is linked, through its carbon atom at the 2' position:
either to a phosphoglyceryl group,
or to a phosphate group, which is joined to the carbon at the 5' position of a "modified nucleoside group", in which the direct bond between the carbon at the 2' and 3' positions has been eliminated and the carbons at the 2' and 3' positions are respectively bearers of aldehyde groups or of alcohol groups, possibly esterified.

These various aspects of the invention are preferably achieved through novel oligonucleotides comprising a chain containing n nucleoside units, identical or different, n being greater than or equal to 2, these nucleoside units being connected by 2'→5' linkages, which comprise a group of linkages containing at least one phosphorus atom, and in which:

the first nucleoside unit of the above-said chain is linked, through its carbon at the 5' position, to phosphate groups and one of the oxygen atoms of at least one of the phosphate groups, which oxygen atom connected only to the phosporus of the phosphate groups and not taking part in the linkage between two phosphate groups, is replaced by a sulfur atom, an atom of selenium or an NH group, and/or one at least of the linkages between two adjacent phosphate groups comprises an NH group or a sulfur atom;

and possibly the "last nucleoside unit" of the above-said chain is joined, through its carbon atom at the 2' position:
either to a phosphoglyceryl group;
or to a phosphate group, which phosphate group is connected through the carbon at the 5' position of a "modified nucleoside group", in which the direct linkage between the carbon at the 2' and 3' positions has been eliminated, and the carbon atoms at the 2' and 3' positions are bearers of aldehyde groups, or of alcohol groups, possibly esterified.

A nucleoside unit denotes a compound constituted by a pentose linked to a purine or pyrimidine base, in which the pentose can be in the pyran or furan form.

In the rest of the description, the formulae will represent the pentoses generally in furan form.

The nucleoside units are according to the invention advantageously constituted by adenosines, adenosine denotes the compound constituted by ribose linked to adenine and may be represented by the formula:

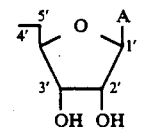

in which the ribose is in furan form, but may also be in pyran form and in which A represents adenine.

Within the scope of the invention, adenine denotes the molecule represented by the following formula:

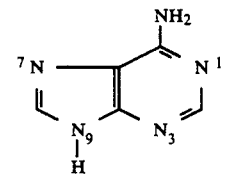

The nucleoside units according to the invention may also be constituted by adenosine derivatives, adenosine derivatives denoting the compound constituted by ribose, joined to an adenine derivative. Among these derivatives of adenine, may be mentioned those of the following formula:

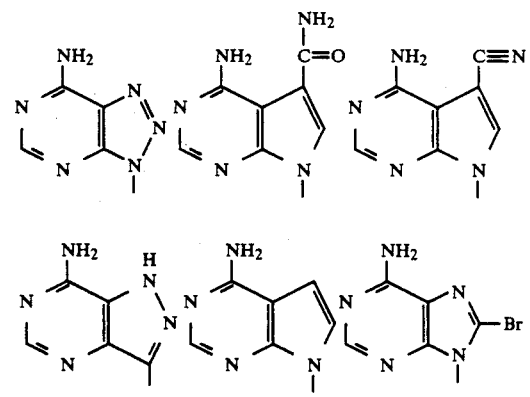

The corresponding adenosine derivatives will be respectively denoted by 8-azaadenosine, sagivamycin toyocamycin, formycin, tubercidine, 8-bromo-adenosine.

The number of nucleoside units constituting the oligonucleotides of the invention is not limited within the above values, provided that the oligonucleotides obtained can be associated with a physiologically acceptable vehicle.

This number can rapidly be limited to the extent that the increase in this number and the corresponding more difficult synthesis would not be supported by a sufficient increase in activity.

The number of nucleoside units should be selected so that the molecular weight is preferably comprised between 1 500 to 5 000 daltons.

In a preferred class of oligonucleotides according to the invention, the value of n is not higher than 10, and is preferably 7 or 8.

The oligonucleotides in which the value of n is 3 or 4 are particularly preferred.

In a preferred class of oligonucleotides according to the invention, the first nucleoside unit is linked to one or several phosphate groups.

Preferably, the number of these phosphate groups is 1 to 3.

In a preferred class of compounds of the invention, the first nucleoside unit is linked to the following phosphate groups:

$$-O-\overset{O}{\underset{OR'}{\overset{\|}{P}}}-OH, \quad -O-\overset{O}{\underset{OR'}{\overset{\|}{P}}}-O-\overset{O}{\underset{OR''}{\overset{\|}{P}}}-OH,$$

$$-O-\overset{O}{\underset{OR'}{\overset{\|}{P}}}-O-\overset{O}{\underset{OR''}{\overset{\|}{P}}}-O-\overset{O}{\underset{OR'''}{\overset{\|}{P}}}-OH, \quad -O-\overset{O}{\underset{OR'}{\overset{\|}{P}}}-CH_2-\overset{O}{\underset{OR''}{\overset{\|}{P}}}-OH$$

in which R', R'', R''' represent, independantly of one another:
a hydrogen atom,
an alkyl radical having from 1 to 4 carbon atoms, in particular methyl,
an ethyl radical substituted at the beta position by a cyano, aryl or arylsulfonyl group,
a trihalogenoethyl radical.

In a preferred class of compounds according to the invention, the linkage 2'→5' joining two nucleoside units and comprising at least one phosphorus atom is a phosphodiester linkage, a phosphotriester linkage, or an alkylphosphonate linkage.

The linkage 2'→5' phosphodiester which joins two adjacent nucleoside units in the oligonucleotides according to the invention may be represented as follows:

[structure with base, 2', O-P(=O)(OH)-O-5']

The phosphotriester 2'→5' linkage which joins two adjacent nucleoside units in the oligonucleotides of the invention may be represented as follows:

[structure with base, 2', O-P(=O)(OR$_1$)-O-5']

in which $R_1$ represents an alkyl radical having from 1 to 4 carbon atoms;
an alkyl radical having from 1 to 4 carbon atoms, in particular methyl,
an ethyl radical substituted at the beta position by a cyano, aryl or arylsulfonyl group,
a trihalogenoethyl radical.

The phosphonate 2'→5' linkage which joins two adjacent nucleoside units in the oligonucleotides according to the invention may be represented as follows:

[structure with base, 2', O-P(=O)(R$_2$)-O-5']

in which $R_2$ can represent an alkyl having from 1 to 4 carbons, in particular methyl.

By convention, in an oligonucleotide according to the invention containing n nucleoside units, below, the nucleoside unit of rank n, when the last element of the chain is a phosphoglyceryl group, will be denoted by the expression "last nucleoside unit".

In this case, the oligonucleotide according to the invention will be denoted by (2'-5') (A)$_n$PGro.

When the last element of the oligonucleotide according to the invention is:
either a nucleoside group of the formula:

[furanose ring structure with O, A, OH, OH]

A having the above-indicated meanings;
or a "modified nucleoside group" as defined below; the definitions nucleoside unit of rank n−1 will be denoted by the expression "last nucleoside unit" by convention.

By "modified nucleoside group" is defined a nucleoside group in which:
the direct linkage between the carbon 2' and the carbon 3' joining the linkage directly has been eliminated and may be represented by the following formula:

[structure with 5', 4', 3', 2', 1', O, A]

in which the pentose is in furan form, but may also be in pyran form and in which A represents adenine or a derivative of adenine as defined above;

the carbons at the 2' and 3' positions are bearers of aldehyde functions or of alcohol functions, optionally esterified; in the case where the carbons at the 2' and 3' positions bear alcohol functions, the oligonucleotides according to the invention will be denotable by (2'-5') $(A)_n$Ox Red.

The oligonucleotides according to the invention may be represented by the following formula (I):

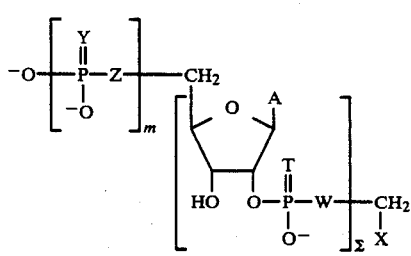

(I)

in which:

Y and T, identical or different, represent independantly of one another, O, S, Se or NH;

Z and W, identical or different, represent independantly of one another, O, S or NH;

X represents:

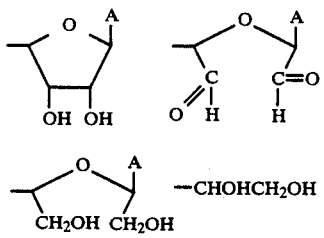

A represents adenine or one of its derivatives as defined above;

$\Sigma$ is a whole number equal to:

n when X represents -CHOHCH$_2$OH;

n−1 when X is different from -CHOHCH$_2$OH n being a whole number greater than or equal to 2;

m is a whole number equal to 0 and preferably greater than or equal to 1; provided that:

either one at least of the two elements Y or Z is different from oxygen;

or X represents:

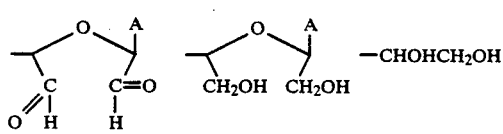

or one at least of the elements Y or Z is different from oxygen and X represents:

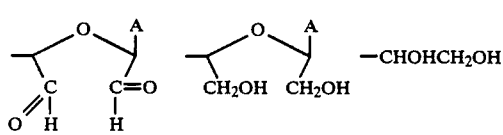

A preferred class of oligonucleotides according to the invention is constituted by those corresponding to the following formula (I):

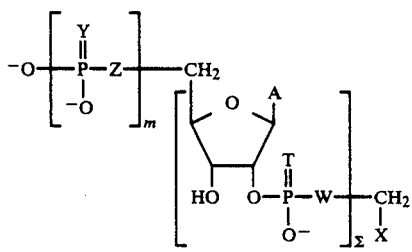

(I)

in which:

Y and T are identical or different and represent O, S, Se, NH;

Z and W are identical or different and represent O, S, NH;

one at least of the elements Y and Z being different from oxygen;

X is selected from the group constituted by:

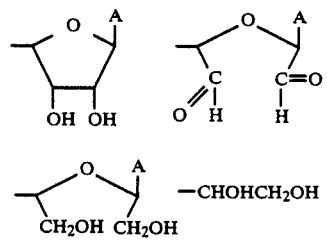

the alcohol functions of these radicals being possibly esterified by R$_3$COOH carboxylic acids, R$_3$ representing an alkyl radical of 1 to 5 carbon atoms, or a phenyl radical:

$\Sigma$ is a whole number equal to:

n when X represents —CHOHCH$_2$OH, n−1 when X represents:

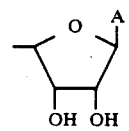

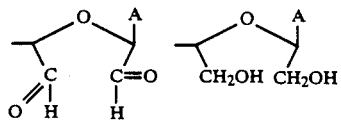

n being a whole number greater than or equal to 2;

m is a whole number greater than or equal to 1;

A is a base selected from among adenine and its derivatives, particularly those of the formula:

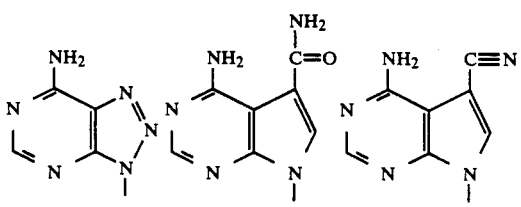

-continued

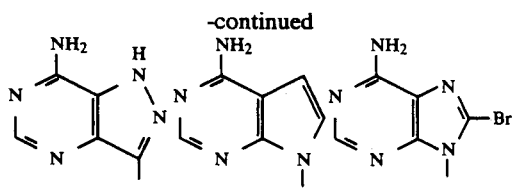

In a preferred clss of oligonucleotides according to the invention, the number m varies preferably from 1 to 3.

Among the groups connected to the first nucleoside unit and of formula:

one at least is such that Y represents Se, S or NH and/or Z represents S or NH, and the other groups:

representing phosphate groups.

In a preferred class of oligonucleotides according to the invention, X represents S, and Z represents O.

A preferred class of oligonucleotides according to the invention is that in which X is either a modified nucleoside group which can be represented by:

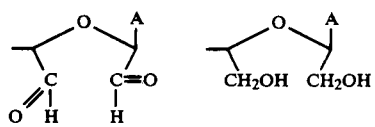

or the group —CHOHCH$_2$OH.

The alcohol functions of the radicals:

are possibly esterified by an R$_3$COOH carboxylic acid, in which R$_3$ represents an alkyl radical of 1 to 5 carbon atoms or a phenyl radical.

A preferred class of oligonucleotides according to the invention is constituted by those of the following formula (II):

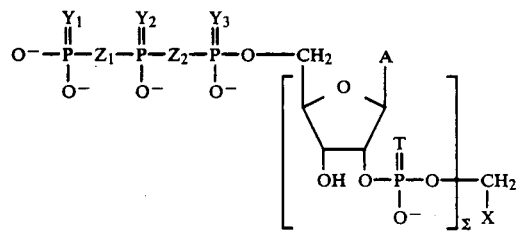

(II)

in which:

$Y_1$, $Y_2$, $Y_3$, T are identical or different and represent O, S, Se, NH;

$Z_1$ and $Z_2$ are identical or different and represent O, S, NH; one at least of the elements $Y_1$, $Y_2$, $Y_3$, $Z_1$, $Z_2$ being different from oxygen;

X is selected from the group constituted by:

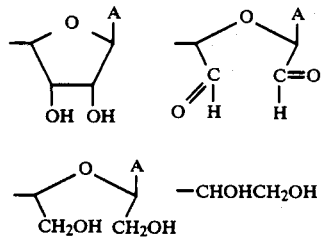

the alcohol functions of these radicals being possibly esterified by R$_3$COOH, carboxylic acids, R$_3$ representing in alkyl radical of 1 to 5 carbon atoms or a phenyl radical;

represents a whole number equal to n, when X represents —CHOHCH$_2$OH, and Σ represents a whole number equal to n−1 when X is a different from —CHOHCH$_2$OH, n being a whole number greater than or equal to 2;

—A is a base selected from among adenine and its derivatives, particularly those of the formula:

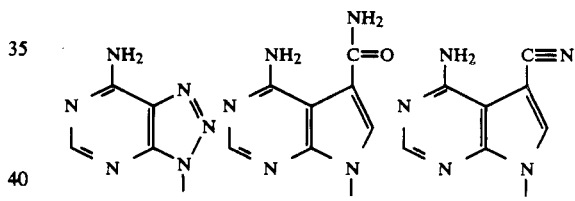

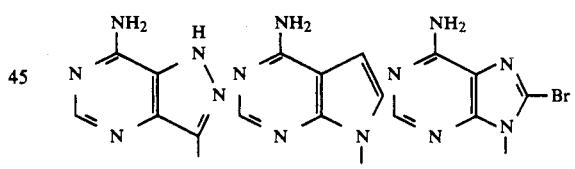

The phosphorus of the group:

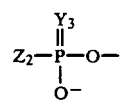

will be called alpha phosphorus.
The phosphorus of the group:

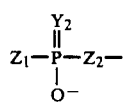

will be called beta phosphorus.
The phosphorus of the group:

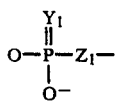

will be called gamma phosphorus.

Within the class of oligonucleotides of formula (II), a preferred class of oligonucleotides according to the invention is constituted by the oligonucleotides of formula (III):

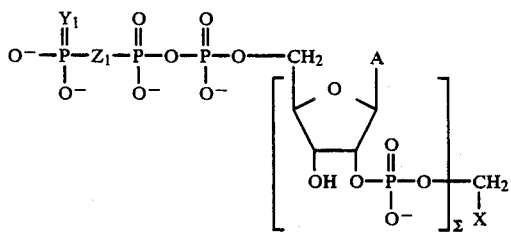

in which:
Y₁ represents S, Se, or NH;
Z₁ represents O, NH or S;
Σ, X and A having the above-indicated meanings.

Within this class of oligonucleotides, a preferred class of oligonucleotides is constituted by those in which:
X represents: either:

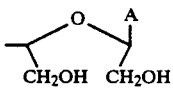

A representing adenine; or:
—CHOHCH₂OH.

Another preferred class of oligonucleotides according to the invention is constituted by those of the following formula (IV):

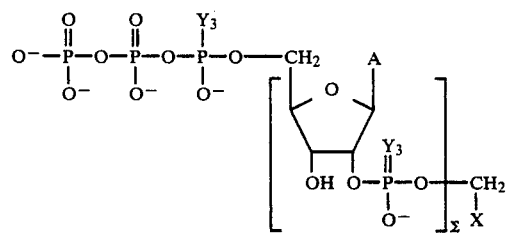

in which:
Y₃ represents S, Se or NH,
Σ, X and A having the above-indicated meanings.

Within this oligonucleotide class, a preferred class of oligonucleotides according to the invention is constituted by those in which:
X represents: either:

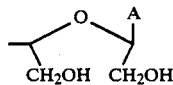

A representing adenine; or:
—CHOHCH₂OH.

Another class of preferred oligonucleotides according to the invention is constituted by that of the following formula (V):

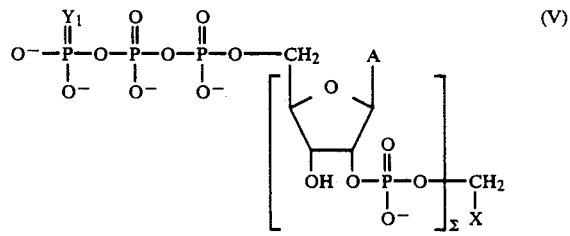

in which:
Y₁ represents Se, S or NH;
Σ, X and A having the above-indicated meanings.

Within this class, a preferred class of oligonucleotides according to the invention is constituted by those in which:
X represents: either:

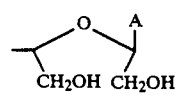

A representing adenine; or:
—CHOHCH₂OH.

Another preferred class of oligonucleotides according to the invention is constituted by those of the following formula (VI):

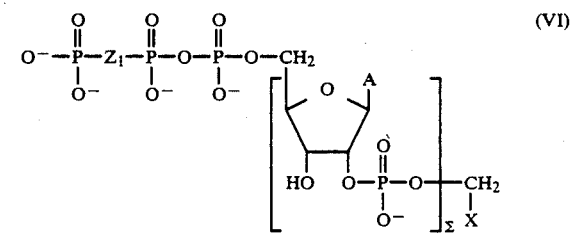

in which:
Z₁ represents S or NH;
Σ, X and A having the above-indicated meanings.

Within this class, a preferred class of oligonucleotides is constituted by those in which:
X represents: either:

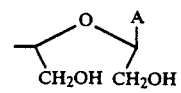

A representing adenine; or:
—CHOHCH₂OH.

Another preferred class of oligonucleotides according to the invention is constituted by those of the following formula (VII):

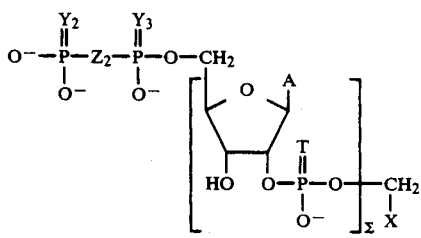 (VII)

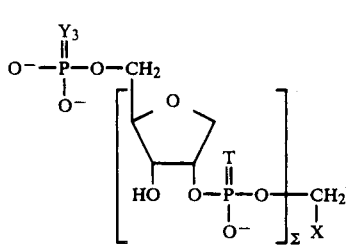 (VIII)

in which:

$Y_2$, $Y_3$, T are identical or different and represent O, S, Se, NH;

$Z_2$ represents O, S, NH; one at least of the elements $Y_2$, $Y_3$, $Z_2$ being different from oxygen;

X is selected from a group constituted by:

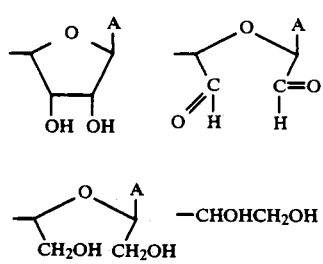

Σ, is a whole number equal to n, when X represents —CHOHCH$_2$OH and is a whole number equal to n−1, when X is different from —CHOHCH$_2$OH, n being a whole number varying from 2 to 10;

A is a base selected from among adenine and its derivatives, particularly those of the formula:

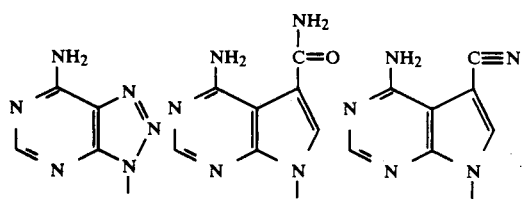

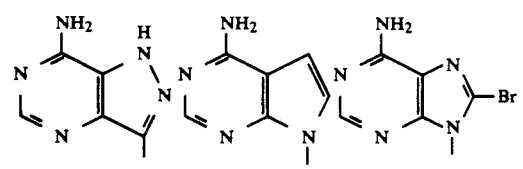

Within this class of nucleotides a preferred class is constituted by those in which T represents oxygen.

Another preferred class of the oligonucleotides according to the invention is constituted by those of the following formula (VIII):

in which:

$Y_3$ represents S, Se, NH;

T represents O, S, Se, NH;

X is selected from the group constituted by:

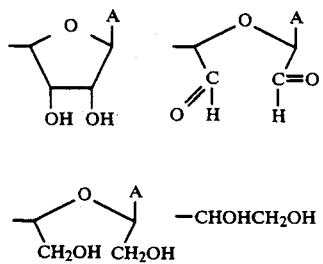

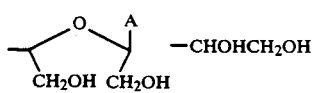

Σ represents a whole number equal to n, when X represents —CHOHCH$_2$OH and a whole number equal to n−1 when X is different from —CHOHCH$_2$OH, n being a whole number varying from 2 to 10;

A is a base selected from among adenine and its derivatives, particularly those of the formula:

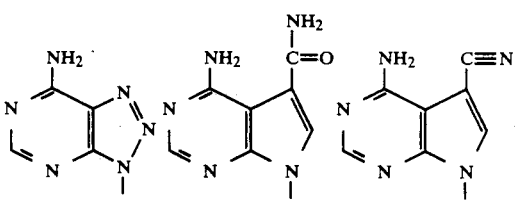

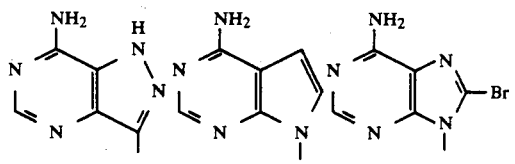

Within this class of nucleotides a preferred class is constituted by those in which T represents oxygen.

Particularly preferred oligonucleotides according to the invention have the formula:

(IX)
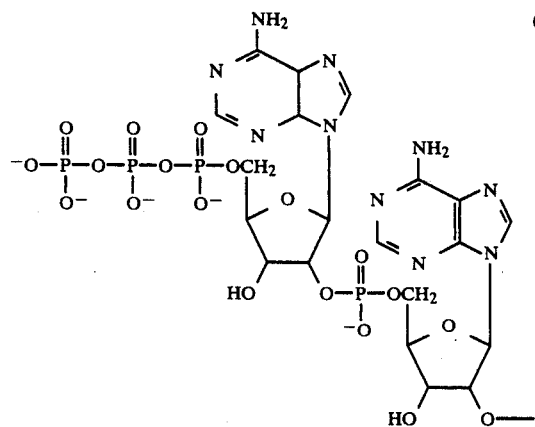
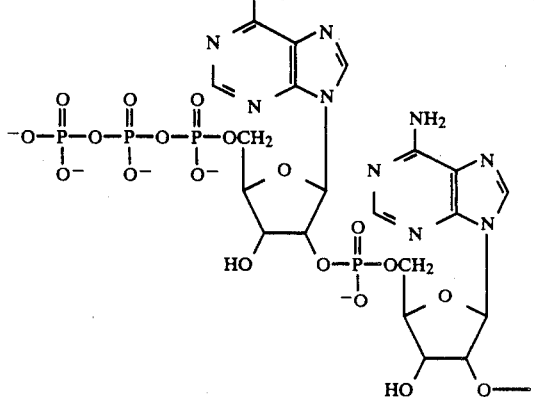
(XI)
-continued
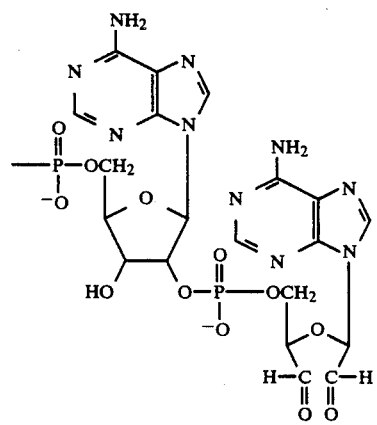
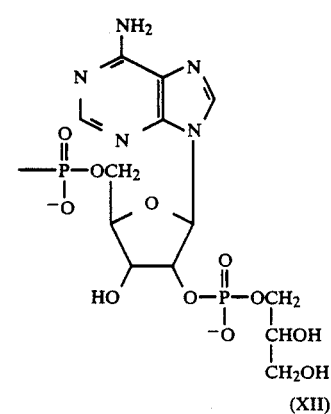
(XII)
(X)
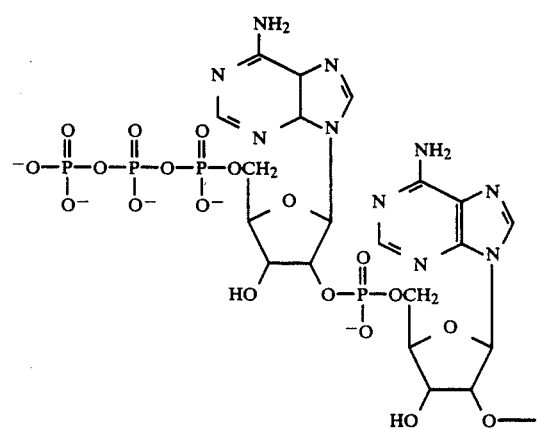
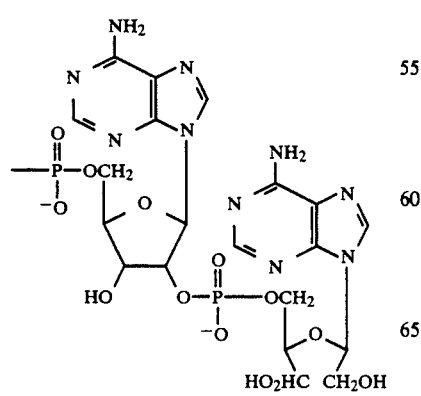
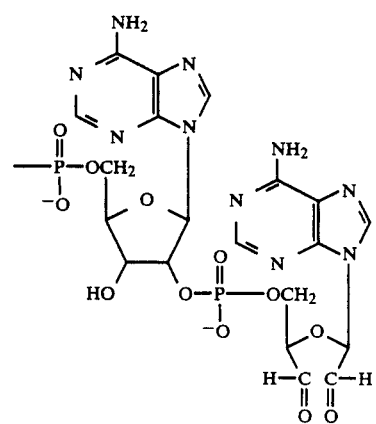

-continued
(XIII)
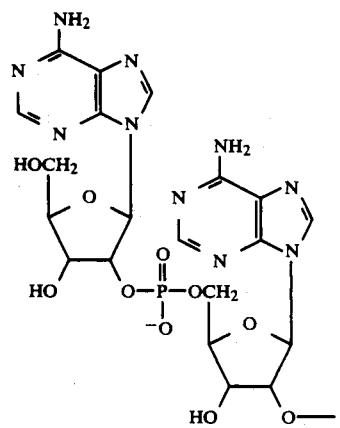
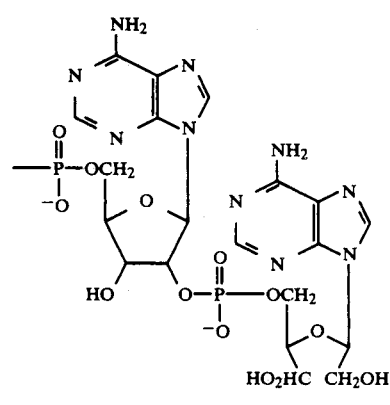
(XIV)
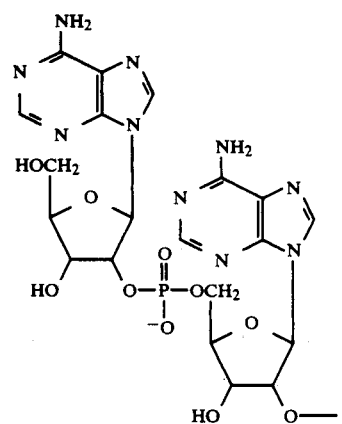
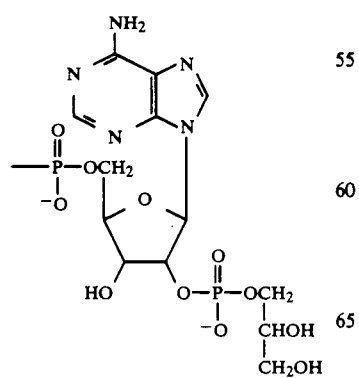
-continued
(XV)
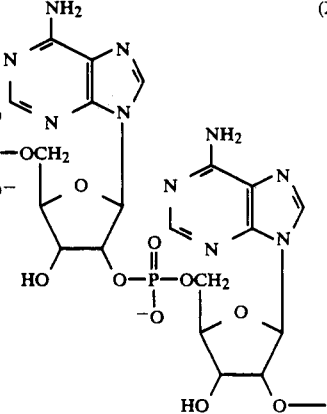
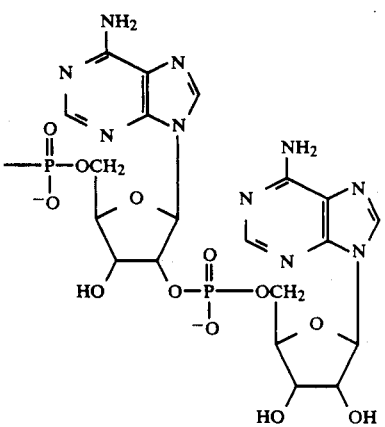
(XVI)
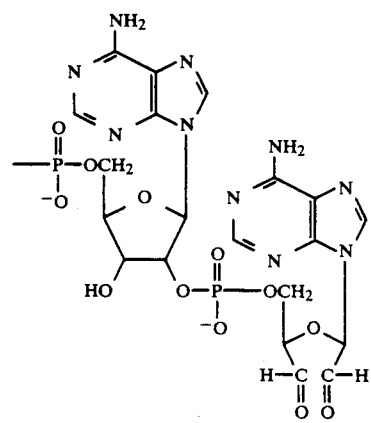

with suitable bases, in particular the quaternary ammonium salts, such as the triethylammonium salt, inorganic salts, such as the sodium salt.

The invention also relates to a process for the preparation of the oligonucleotides.

To prepare the oligonucleotides according to the invention, either a full chemical synthesis, or an enzymatic synthesis followed by chemical modifications may be resorted to.

As regards the chemical synthesis, reference may be made to the procedure described in Methods of Enzymology, 79, 1981, 233-234.

As regards the enzymatic synthesis of the oligonucleotides of formula (I) according to the invention, it comprises:

the polymerisation of compounds of following formula (XIX):

$$\left[ O^- - \overset{Y}{\underset{O^-}{\overset{\parallel}{P}}} - Z \right]_m - CH_2 \underset{OH\ OH}{\overset{O}{\diagup}} A$$
(XIX)

in which:
Y represents O, S, Se or NH;
Z represents O, S, or NH;
one at least of the elements Y and Z being preferably different from oxygen;
m is greater than or equal to 3;
A has the above-indicated meanings;
to obtain a compound of the following formula (Ibis):

$$-O\left[ \overset{Y}{\underset{-O}{\overset{\parallel}{P}}} - Z \right]_m \left[ CH_2 \underset{HO}{\overset{O}{\diagup}} A \underset{O^-}{\overset{T}{\overset{\parallel}{P}}} - W \right]_\Sigma CH_2 \underset{OH\ OH}{\overset{O}{\diagup}} A$$
(Ibis)

in which:
Y and T, identical or different, represent O, S, Se, NH;
Z and W, identical or different, represent O, S, NH;
one at least of the elements Y and Z being preferably different from oxygen;
Σ is a whole number equal to n−1, in being greater than or equal to 2;
m is a whole number greater than or equal to 1;
A has the above-indicated meanings;
and if necessary the following chemical steps namely:

possible oxidation of the glycol group to introduce aldehyde functions on the carbons at the 2' and 3' positions of the last nucleoside unit and to obtain the compound of formula (Iter):

The invention also relates to the salts which can be obtained by reaction of the abovesaid oligonucleotides

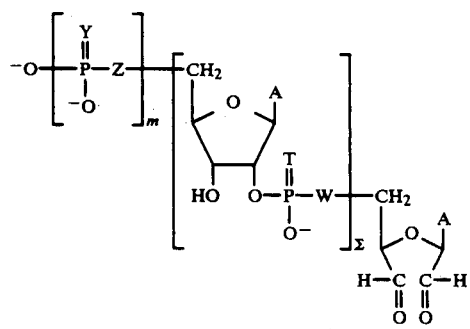
(Iter)

The possible reduction of the two aldehyde functions into alcohol functions to obtain the compound of formula (Iquater):

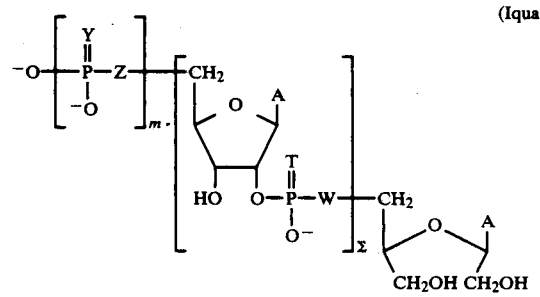
(Iquater)

The possible hydrolysis, under conditions avoiding beta-elimination, to obtain the compound of the following formula (Iquinquies):

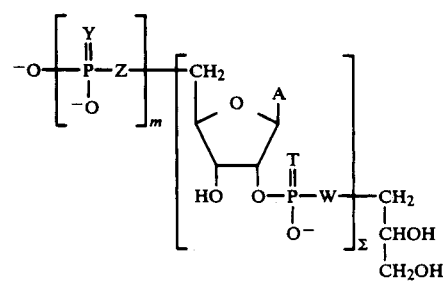
(Iquinquies)

A preferred method of producing oligonucleotides according to the invention of the following formula (XX):

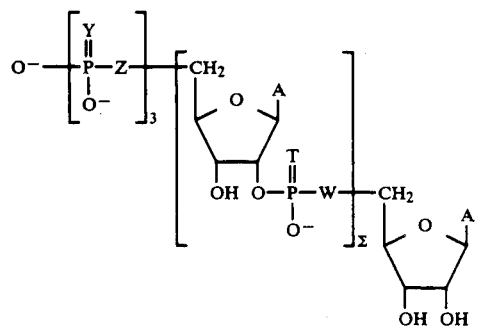
(XX)

in which:

Y and T, identical or different, represent O, S, Se, NH;

Z and W, identical or different, represent O, S, NH;

Y and Z do not simultaneously represent oxygen; Σ is a whole number varying from 1 to 9;

A is a base selected from among adenine or its derivatives, particularly those of formula:

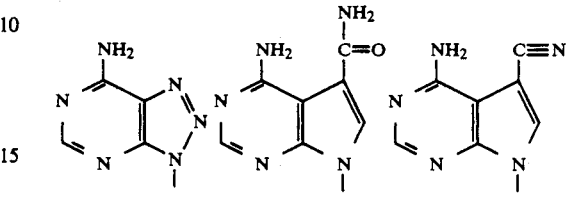

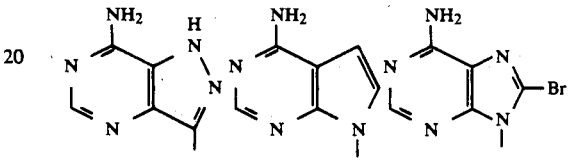

comprises:

1. the polymerisation of a compound of the following formula (XIXbis):

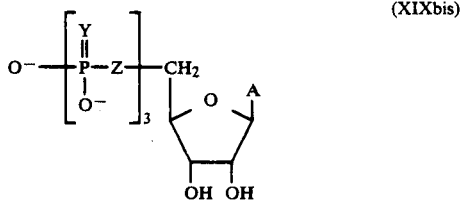
(XIXbis)

in which:
Y represents O, S, or NH;
Z represents O, S, or NH;
Y and Z do not simultaneously represent oxygen;
A has the above-indicated meanings;

2. the possible oxidation of the terminal glycol group, particularly by the periodate ion to convert the glycol into two aldehyde functions and to obtain a compound of the following formula (XXI):

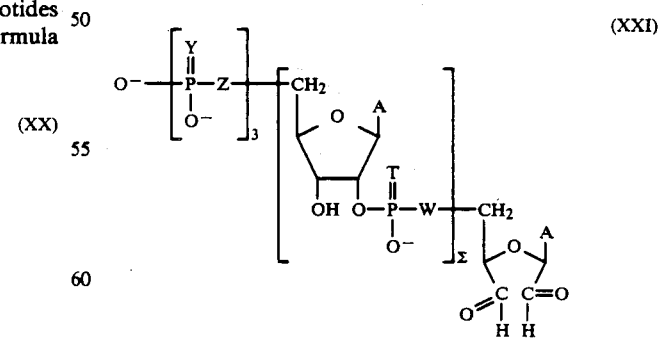
(XXI)

in which Y, Z, T, W, π and A have the above-indicated meanings;

3. the possible reduction of the aldehyde functions, particularly by sodium borohydride to convert the two abovesaid aldehyde functions into alcohol functions and to obtain the compound of the following formula (XXII):

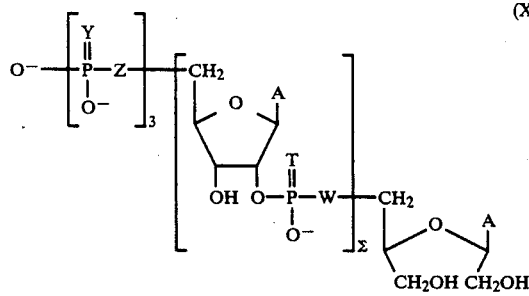

(XXII)

4 the possible hydrolysis, particularly controlled acid hydrolysis, to remove the ribose nucleus and to obtain the compound of the following formula (XXIII):

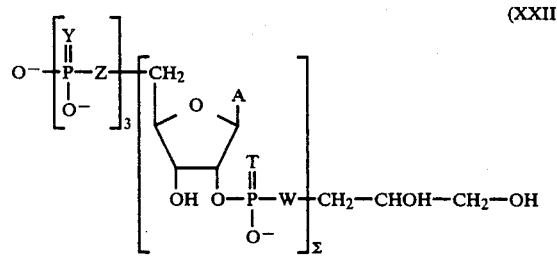

(XXIII)

Among the compounds of the formula (XIX) are available in commerce, those of the following formula (XIXbis):

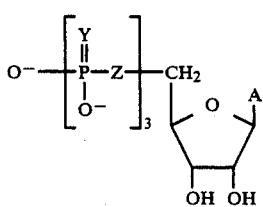

(XIXbis)

in which Y represents sulfur and Z represents oxygen, as well as those in which Y represents oxygen and Z represents the NH group, A representing adenine or one of its derivatives as define above.

The oxidation of the glycol group of the last nucleoside unit to eliminate the direct linkage between the carbon at the 2' position and the carbon at the 3' position and to introduce two aldehyde functions can be carried out by periodic acid under rigorously controlled pH conditions to avoid beta elimination.

The expression "rigorously controlled pH conditions" means the maintenance of the reaction medium at pH 4.0, at 0°–4° C. and in darkness.

The reduction of the aldehyde functions into alcohol functions can be effected by sodium borohydride. The hydrolysis to convert:

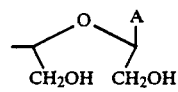

into a —CHOHCH$_2$OH group is preferably a controlled acid hydrolysis, carried out according to conventional methods.

A process for the obtaining according to the invention of the oligonucleotides of the following formula (V):

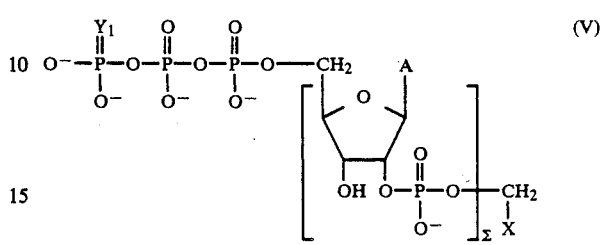

(V)

in which:
$Y_1$ represents NH, Se, S;
X represents:

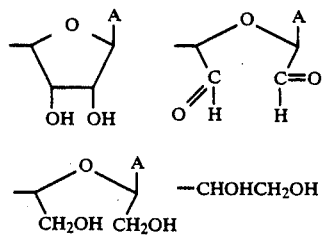

$\Sigma$ is a whole number equal to n, when X represents —CHOHCH$_2$OH, n−1 when X is different from —CHOHCH$_2$OH, n varying from 2 to 10;
is characterised in that the compounds of the following formula (XXIV):

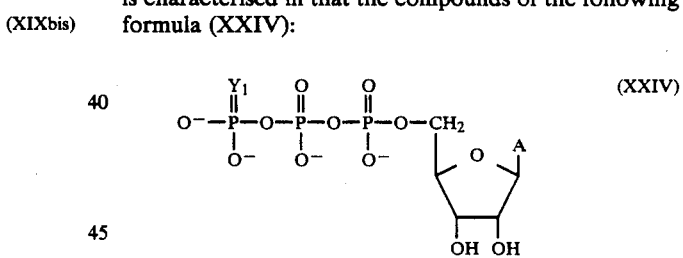

(XXIV)

is polymerised and the steps 2°, 3° and 4° are carried out as indicated above.

Within the class of process which have just been defined, a process according to the invention for producing oligonucleotides of the following formula (Vbis):

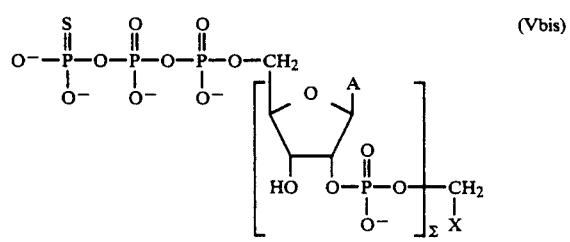

(Vbis)

in which:
$\Sigma$, X have the previously indicated meanings;
A has the previously indicated meaning, and preferably represents adenine;

is characaterized in that a compound of the following formula (XXIVbis):

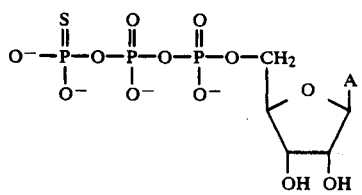

(XXIVbis)

is polymerised and the steps 2, 3 and 4 are carried out as indicated above.

A process according to the invention for producing oligonucleotides of the following formula (VI):

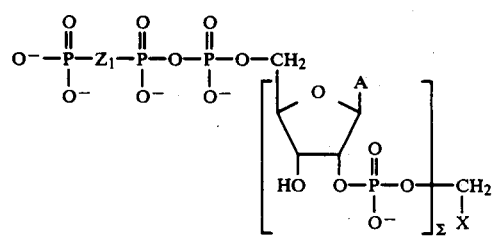

(VI)

in which:

$Z_1$ represents NH or S;

X is selected from the group constituted by:

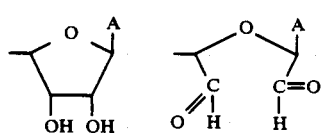

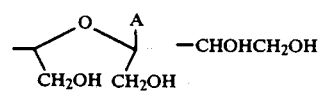

$\Sigma$ is a whole number equal to 1, when X represents —CHOHCH$_2$OH and equal to n−1 when X is different from CHOHCH$_2$OH, n varying from 2 to 10: is characterised in that the compound of the following formula (XXV):

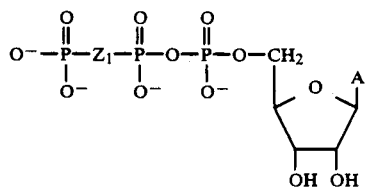

(XXV)

in which $Z_1$ represents S or NH and A has the above-indicated meaning, is polymerised: and the steps 2, 3 and 4 are carried out as indicated above.

A process for obtaining oligonucleotides according to the invention of the following formula (IV):

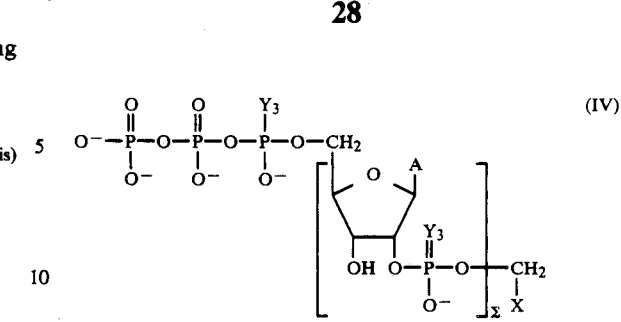

(IV)

in which:

$Y_3$ represents NH, S or Se;

$\Sigma$, X and A have the above-indicated meanings;

is characterised in that the compound of the following formula (XXVI):

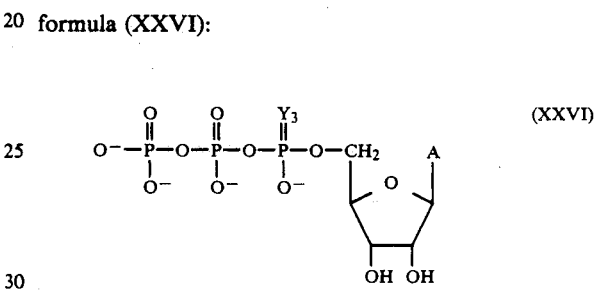

(XXVI)

in which:

$Y_3$ represents S, Se, NH;

A has the above-indicated meanings, is polymerised; and the steps 2, 3 and 4 are carried out as indicated above.

EXAMPLE 1

This example relates to the preparation of oligonucleotides (2'-5')(A)$_n$ synthesised enzymatically and modified chemically. These compounds may be represented by the following formulae:

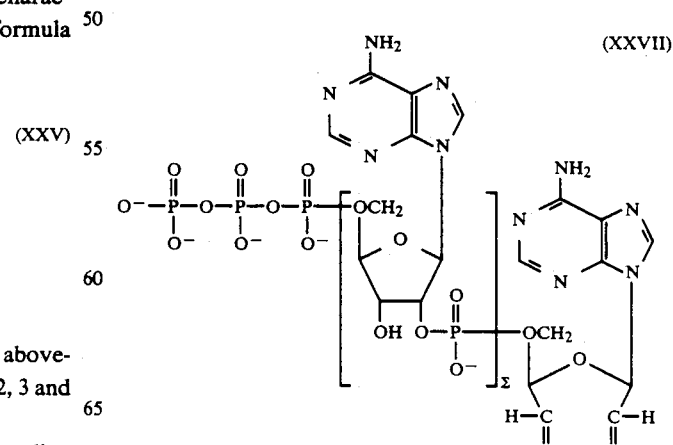

(XXVII)

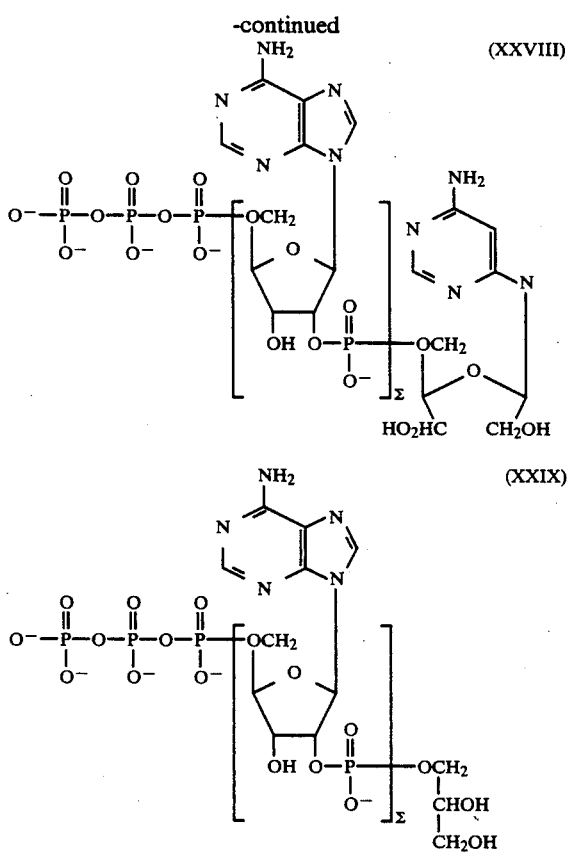

and their corresponding dephoshporylated derivatives.

MATERIALS AND METHODS

Materials

The media come from Eurobio (Paris) and the serums from Flow Laboratories.

For example interferon of human leucocytes (Hu IFN α) purified to a specific activity of $2 \times 10^6$ IU/mg of proteins, is used.

The polyacid ribocytidylic riboinosinic-polyacid [denoted below by the abbreviation poly (rI). poly(rC)] is obtained, for example, from PL Biochemicals. The type III-R bacterial alkaline phosphatase comes from sigma and is preserved at 4° C.

The [$\gamma^{32}$P] ATP (specific activity 2 000 Ci/mM) and the (2'-5')(A)-pCp[$^{32}$p] (specific activity 3 000 Ci/mM) come from Amersham.

The sodium boro [$^3$H] hydride (specific activity 30 Ci/mol) is supplied by the Commissariat a l'Energie Atomique.

The diethylaminoethyl-trisacryl (denoted below by DEAE trisacryl) was obtained from l'Industrie Biologique Française.

Cells and virusas

HeLa cells are kept in monolayers in a medium marketed under the name RPMI 1640, particularly by Laboratoires Eurobio, Paris, completed by 10% (v/v) foetal calf serum, 50 IU/ml of penicillin and 50 μg/ml of streptomycin. L929 cells were grown in a minimum essential medium supplemented with 5% (v/v) of donor horse serum, 3 g/l of bactotryptose phosphate broth, 3.4 g/l of glucose and antibiotics as mentioned above. The Indiana strain of the vesicular stomatitis virus (VSV) was used and allowed to grow in L929 cells.

Ensymatic synthesis of (2'-5')(A)$_n$ of oligoadenylates (2'-5')(A)$_n$ oligoadenylates were synthesised enzymatically by the method described by MINKS et coll. (J. Biol. Chem., 1979, 254, 5 058-5 064).

The preparation of the (2'-5')(A)$_n$ compounds may be summarised as follows.

Cytoplasmic extracts were prepared from HeLa cells treated with 200 units per ml of interferon of human leucocytes for 48 hours. The extract was incubated with 5 mM of ATP and 20 ug/ml of poly(rI).poly(rC) for 2 hours, brought to boiling for 3 min at 100° C. and centrifuged at 10 000 g for 10 min. [$\gamma^{32}$p] (2'-5')(A)$_n$ oligomers were synthesised by incubating cellular extracts with [$\gamma-^{32}$p] ATP under the same conditions.

Fractionation of the (2'-5')(A)$_n$ oligoadenylates

Approximately 4 000 units of optical density at 260 nm of (2'-5')(A)$_n$ were synthesised, that is to say 100 μmoles, n ranging from 2 to 15 (for subsequent fractionation) in extracts of HeLa cells treated with interferon at 37° C. for 2 hours as described above. The proteins were precipitated by incubation of the mixture at 100° C. for 5 min and centrifugation at 15 000 x g for 10 min. The supernatant liquor was diluted 3 times with water and adjusted to pH 805 with 0.1 M KOH before being charged onto a column (2.5×64 cm) of trisacryl M DEAE, equilibrated with a buffer at pH 8.5 of 0.25 M triethylammonium bicarbonate. The column was washed with 1 500 ml of this buffer and the (2'-5')(A)$_n$ loigoadenylates were eluted with a linear gradient (1 500 ml/1 500 ml) at pH 8.5 of 0.125-0.45 M triethylammonium bicarbonate. The oligomers at the individual peaks were identified by high performance liquid chromatography (HPLC). The fractions were concentration under vacumm under reduced pressure and co-evaporated with water several times, in order to remove the triethylammonium bicarbonate buffer. Amounts in mg of each of the oligomers can be obtained in purified form and checked by HPLC.

Synthesis and purification of the nuclei or "cores" of (2'-5')(A)$_n$

The dephosphorylated oligoadenylates which have also been denoted by "cores" or nuclei (400 units of A$_{260}$) obtained by enzymatic digestion of (2'-5')(A)$_n$ of alkaline phosphatase were fractionated by ion exchange chromatography on a column (1.5×25 cm) of DEAD-trisacryl M. Each dephosphorylated oligoadenylate was obtained in pure form by elution of the column with a linear gradient (300 ml/300 ml) of buffer at pH 8.5 of triethylammonium bicarbonate (0-100 mM).

Chemical modification of oligoadenylates (2'-5') (A)$_n$

The oxidation was carried out, by means of periodate, of the (2'-5')(A)$_n$ for 15 hours under controlled conditions, in order to avoid beta-elimination. Conventionally, 100 μl of sodium metaperidate 16 mM in an 0.2 M sodium acetate buffer at pH 4.0 was added to 100 μl of (2'-5')(A)$_n$ 1 mM in distilled water at 4° C. The mixture was shaken at 4° C. in darkness for 15 hours. The excess periodate was destroyed immediately after the oxidation phase with 10 μl of ethylene glycol and the dialdehyde derivative at the 2', 3' position, according to the invention, corresponding to the (2'-5')(A)$_n$ compound was reduced at 4° C. for 5 hours by 100 μl of 0.1 M sodium borohydride in an 0.1 M borate buffer at pH 9.0. In certain cases, the dialdehyde at the 2', 3' position is reduced with sodium boro[$^3$H] hydride. The mixture was then acidified with 0.1 M acetic acid and it was desalted on a Sephadex G-15 column. The O-phosphoglycerylated derivative according to the invention of the (2'-5')(A)$_n$ compound was obtained by controlled acid hydrolysis of the riboseoxygen linkage with 0.005 M sulfuric acid at 80° C. for 30 minutes. The 2'-5' oligoadenylates according to the invention which include a terminal O-phosphoglycerylated group will be denoted below by (2'-5')(A)$_n$PGro.

The diagram below summarsies, by way of example, the principal chemical modifications effected from the unmodified (2'-5')(A)$_4$ oligoadenylates to obtain the (2'-5')(A)$_4$ oligoadenylates according to the invention.

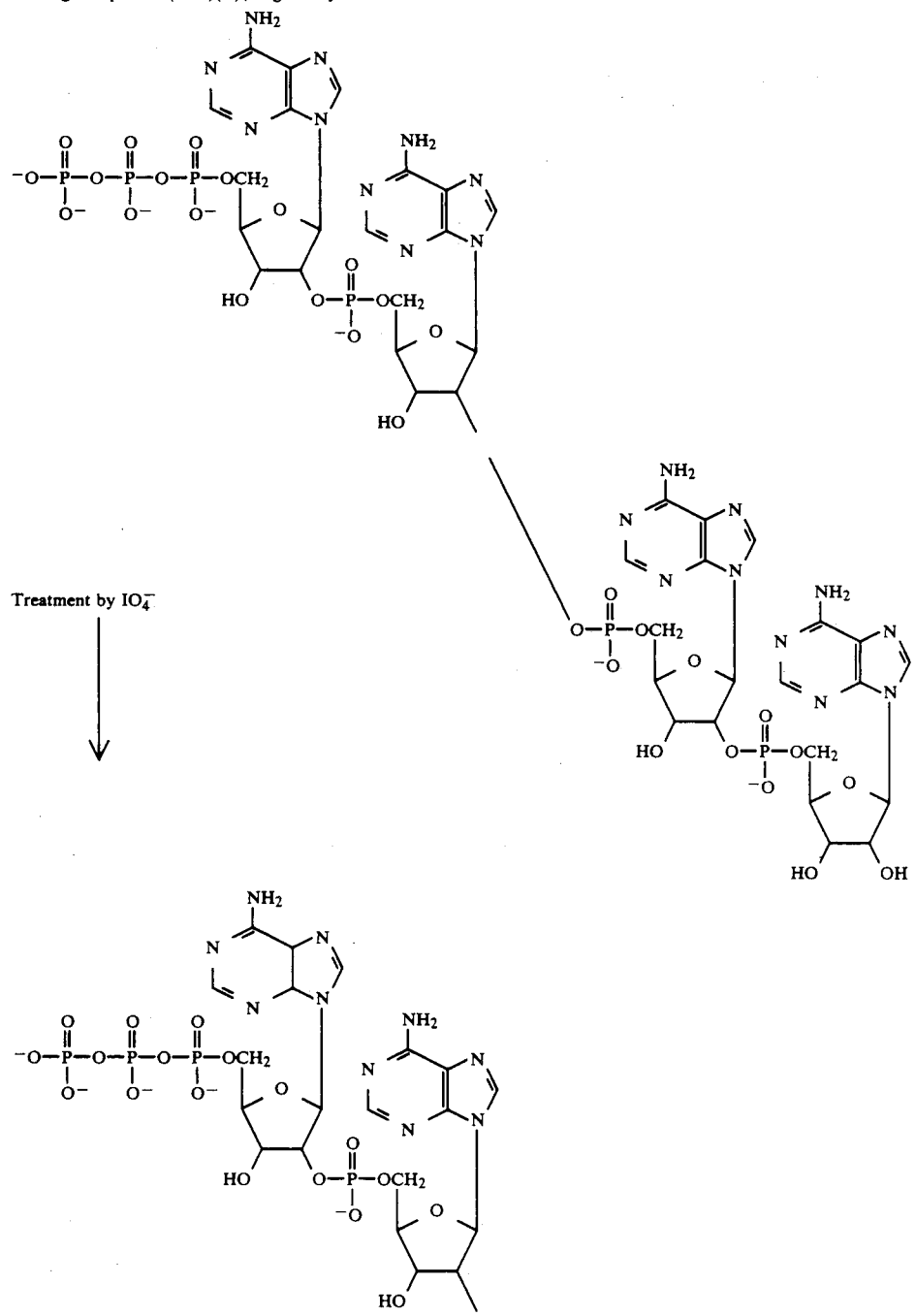

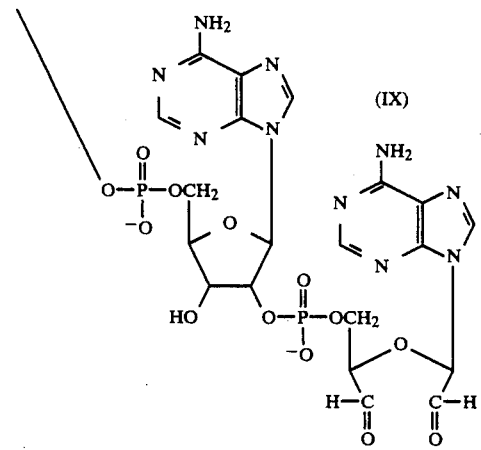

(IX)

The oxidation, for example by periodate ion, of the alpha-glycol group of the $(2'-5')(A)_n$ molecule introduces two aldehyde functions at the 2' and 3' positions, which results in compound (IX).

The two aldehyde functions were reduced, for example, with sodium borohydride into two alcohol functions, which leads to the compound (X).

Compound of formula (IX):

Treatment with BH$_4$Na

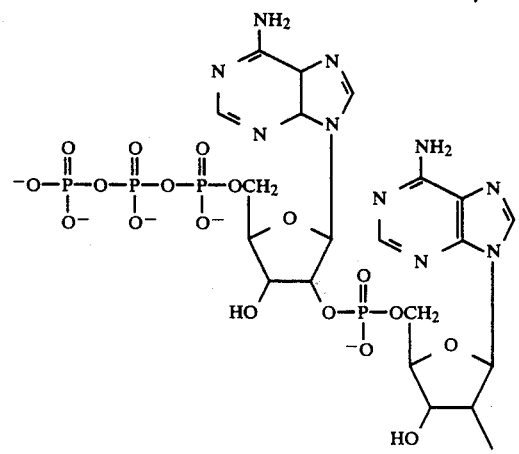

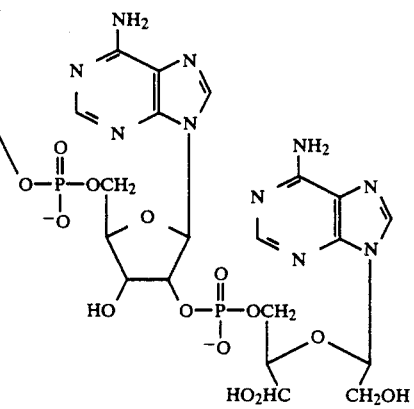

Compound of formula (X): <u>Controlled acid hydrolysis</u> →

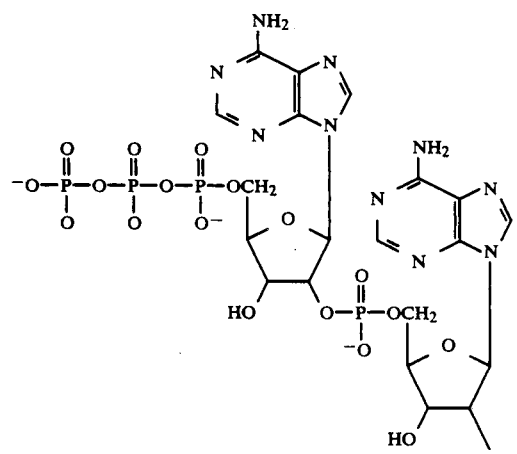

(XI)

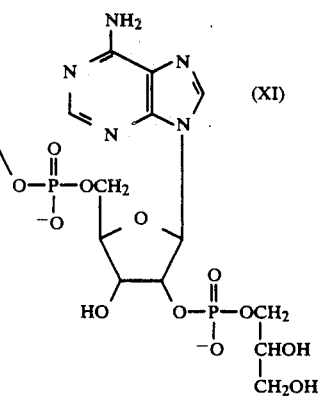

The controlled acid hydrolysis with, for example, dilute sulfuric acid gives a (2'-5') oligoadenylate including a 2'-phosphoglycerated terminal group. The dephosphorylated nuclei corresponding to the compounds of formulae (IX), (X), (XI) are obtained by treatment of the latter, with bacterial alkaline phosphatase.

The compounds of the following formulae were thus respectively obtained:

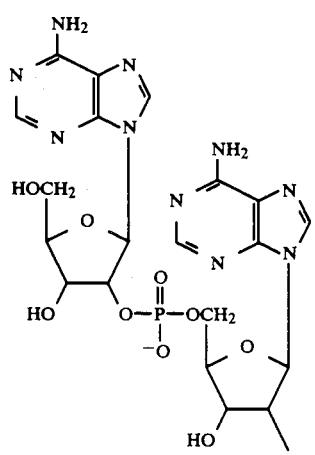

(XII)

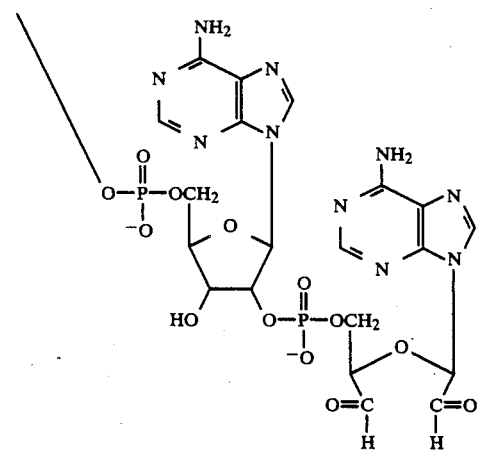
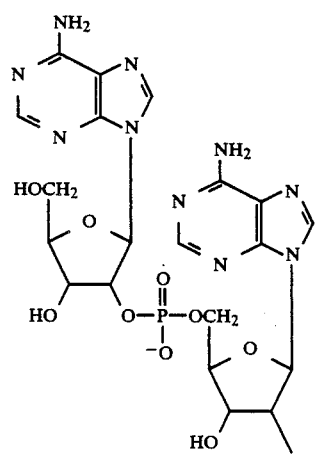
(XIII)
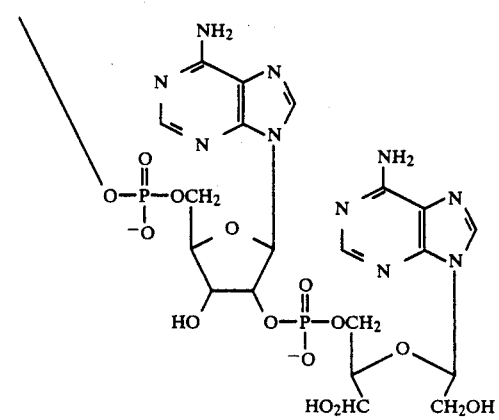

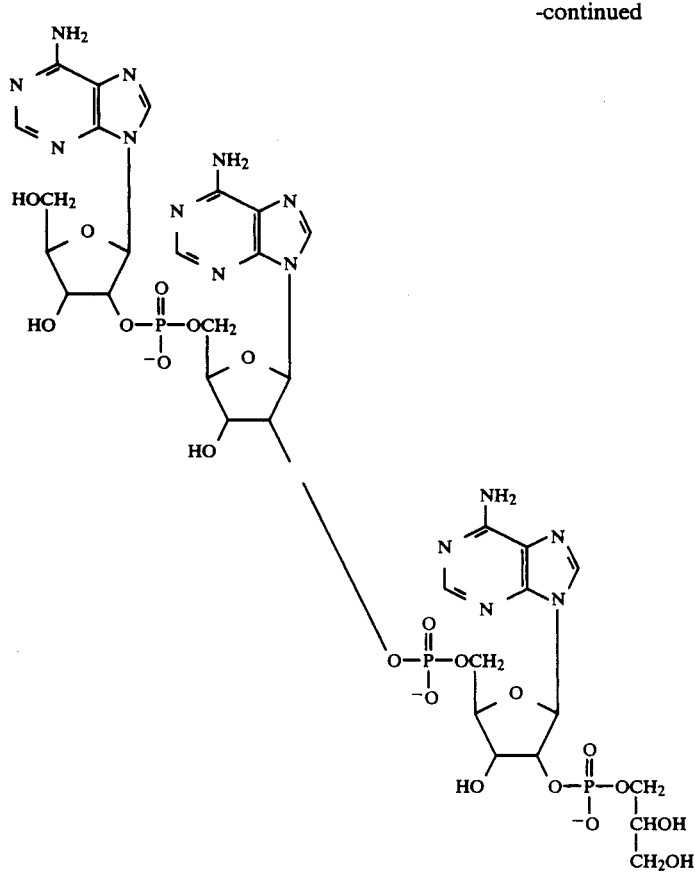

(XIV)

Analysis by high performance liquid chromatography of phosphorylated and unphosphorylated (2'-5')(A)$_n$s and of their O-phosphoglycerylated derivatives The (2'-5')(A)$_n$ oligoadenylates, the (2'-5')(A)$_n$-PGro (2'-O-phosphoglycerylated derivative of (2'-5')(A)$_n$) and the corresponding dephosphorylated oligoadenylates (nuclei) were isolated and characterised on a column marketed under the name μBondapak C in an aluminium phosphate buffer (Brown R.E. et coll., 1981, Methods Enzymol. 78B, 208–216 et Knight M. et coll., 1980, Nature, 288, 189–192). The column was equilibrated with a 50 mM ammonium phosphate buffer at pH 7.0 for the separation of the phosphorylated (2'-5')(A)$_n$ or with a 4mM ammonium phosphate buffer at pH 6.5 for the separation of the dephosphorylated nuclei and it was eluted for 25 minutes with 25 ml of an 0–50% linear gradient of methanol/water (1:1 v/v). All the separations were carried out with an HPLC chromatograph marketed under the name Varian 5 000.

Analysis by high voltage electrophoresis of (2'-5')(A)$_n$ oligoadenylates and their degradation products The individual (2'-5')(A)$_n$ oligoadenylates and their degradation products such as inorganic phosphates (Pi), ATP and AMP were separated by electrophoresis on paper marketed under the name Whatman DE81 in 8.7% (v/v) formic acid at pH 1.8 for 0.5 to 6 hours at 60 V/cm in a high voltage electrophoresis apparatus marketed under the name Gilson. The locations of the radioactive components were marked and they were quantified by autoradiography with a film marketed under the name Kodak X-Omat AR.

Activity of the phosphodiesterase in the HeLa cell extracts

The stability of the (2'-5')(A)$_n$s and of the analogous nuclei according to the invention was determined in a HeLa cell extracts by measuring the disappearance of the oligonucleotides. The (2'-5')(A)$_5$ (5 μl) was incubated to the final concentration of 0.02 mM with 5 μl of HeLa cellular extracts (22 mg of proteins per ml) in the presence of 4-(2-hydroxyethyl)-1-piperazine ethane sulfonic acid (Hepes) 20 mM at pH 7.6 of magnesium acetate 2.5 mM, of 33 mM ammonium chloride, of dithiothreitol and 1 mM phenylmethylsulfonyl fluoride (buffer 1). The reaction was stopped by heating to 100° C. for 2 minutes and it was centrifuged at 10 000 Xg for 10 minutes. The (2'-5')(A)$_3$ (1 nM) was added to with the supernantant liquor as internal reference and the residual products were quantified by HPLC as described above.

Activity of phosphates in HeLa cell extracts

The (2'-5')(A)$_n$ oligoadenylates and their analogs according to the invention were incubated in HeLA (5 μl) cellular extracts for different periods of time in 20 μl tests, in the above-defined buffer 1 (cf. test with phosphodiesterase) or in the same buffer completed with ATP 1 mM, GTP (guanosine triphosphate) 0.1 mM, CTP (cytosine triphosphate) 0.6 mM, creatine phosphate 100 mM, creatine phosphokinase in the proportion of 160 μg/ml and all 20 aminoacids in the proportion of 500 uM each (buffer 2). The reaction was stopped by heating at 100° C. for 20 minutes, the proteins precipitated were removed by centrifugation at 10

000 Xg for 10 minutes. The activity of the phosphatase was determined by measuring the disappearance of [γ-$^{32}$p]($2'$-$5'$)(A)$_n$ and the concomitant appearance of $^{32}$Pi, released after high voltage electrophoresis or by measuring the accumulation of oligoadenylate nuclei, by high performance liquid chromatography.

Cellular Micro-injection

HeLa cells were cultivated on small fragments of glass (2 mm2) at densities which permitted about 200 cells to be attached to each of the glass fragments as described in Huez G. et coll., 1981, Proc. Natl Acad. Sci., 78, 908–911. Micro-injections were carried out according to the method originally described by Graessmann (1983, Methods Enzymol., 101, 482–492). An average volume of 0.5 nl (approximately 1/10th of the cellular volume) was injected into the cytoplasm of each of the cells with glass micro-pipettes of 0.5–1 μm diameter. The injections were checked under a phase contrast microscope marketed by Leitz-Diavert with a magnification of 320.

Test of Antiviral Activity

The cells were infected at times indicated, generally one hour after the micro-injection, with a vesicular stomatitus virus (VSV) at a multiplicity of 10 for one hour at 37° C. in an RPMI 1640 medium supplemented with foetal calf serum 5% (v/v). The unadsorbed viruses were carefully removed by three washings with RPMI containing 10% foetal calf serum (v/v).

The titer of virus produced 18 hours later was determined by known methods (Stewart W. E. ., 1970, J. Virol., 6, 795–799). To summarise 10$^6$ L929 cells were placed in Petri dishes for tissue culture (2 cm diameter). 24 hours after incubation, 0.05 ml of the dilute virus suspensions (dilution factor 50) were carefully spread on the monolayer of cells. One hour later, the virus suspension was removed by suction and 2 ml of molten agarose (1.6% v/v) was spread in a minimum essential medium completed with 2% (v/v) foetal calf serum on the monolayer of cells. The plates were incubated for 18 hours in an incubator with $CO_2$. The plates were then developed by a 1% (v/v) solution of neutral red in an isotonic buffered phosphate saline solution.

RESULTS

Synthesis and Chemical Modification of ($2'$-$5'$)(A)$_n$ mg amounts of ($2'$-$5'$)(A)$_n$ were synthesised enzymatically in HeLa cell extracts treated with interferon and fractionated in one step by ion exchange chromatography on trisacryl DEAE as previously described. Chemical modifications were then made as indicated above, to obtain the modified ($2'$-$5'$)(A)$_n$s according to the invention.

Stability of ($2'$-$5'$)(A)$_n$ and of its Analogs

In order to test the stability of the compounds according to the invention with respect to 2-phosphodiesterase the ($2'$-$5'$)(A)$_n$ nuclei and their O-phosphoglyceryl derivatives were incubated for 8 hours in extracts prepared either from untreated HeLa cells, or from cells treated with interferon, and their disappearance was followed by high performance liquid chromatography. For the HeLa cellular extracts treated with interferon and according to the results published (Minks M. A., 1979, J. Biol. Chem., 254, 5 058–064; Williams B. R. G. et coll., 1978, Eur. J. Biochem., 92, 455–462; Schmidt A et coll., 1979, Proc. Natl Acad. Sci. U.S.A., 76, 4 788–4 792; Verhaegen-Lewalle M. 1982, Eur. J. Biochem., 126, 639–643), the unmodified nuclei were rapidly degraded. On the contrary, the ($2'$-$5'$)(A)$_n$-PGro nucleus or the nucleus of the ($2'$-$5'$)(A)$_n$ derivative bearing two alcohol functions according to the invention were stable under the same conditions. Similar results were obtained in extracts prepared from cells untreated with interferon.

FIG. 1 relates to the stability of the unmodified ($2'$-$5'$)(A)5 nucleus compared with that of the ($2'$-$5'$)(A)$_4$P-Gro. nucleus.

In abscissae, is shown time, expressed in hours, and in ordinates the percentage of nuclei degraded.

The dephosphorylated nuclei of ($2'$-$5'$)(A)$_n$ (represented by triangles in FIG. 1) and their corresponding $2'$-O-phosphoglyceryl derivatives ($2'$-$5'$)(A) PGro nuclei) (represented by circles in FIG. 1) were incubated with HeLa cellular extracts completed (solid line) or not (dashed line) by 1 mM ATP and an ATP regenerating system.

The nuclei were introduced at an initial concentration of 0.02 mM. The incubations were stopped at the times indicated by boiling and the denatured proteins were removed by centrifugation. The residual nuclei of the supernatant liquor were analysed by HPLC as indicated above.

Antiviral Activity of ($2'$-$5'$)(A)$_n$ Oligoadenylates and of Their Phosphoglycerylated Derivatives To test the biological activity of charged compounds such as ($2'$-$5'$)(A)$_n$ and their analogs according to the invention in intact cells, recourse was had to microinjection with micropipettes, considering that it permits the introduction of predetermined amounts of compounds into the cytoplasm, and without disturbing, significantly, cellular metabolism (Graessmann M. 1983, Methods Enzymol., 101, 482–492).

Table 1 below relates to the antiviral activity of unmodified ($2'$-$5'$)(A)5 and of its $2'$-O-phosphoglycerylated derivatives according to the invention.

TABLE 1

ANTIVIRAL ACTIVITY OF $2'$-O-PHOSPHOGLYCERYL
DERIVATIVES OF THE ($2'$-$5'$)(A)$_n$ COMPOUNDS OF THE
INVENTION [($2'$-$5'$)(A)$_n$ -PGro] COMPARED WITH THE
ACTIVITY OF UNMODIFIED ($2'$-$5'$)(A)$_n$
OLIGOADENYLATES

| Test n° | Compound Tested | Concentration (μm) | Titer of virus (pfu/ 200 cells) | % of control |
|---|---|---|---|---|
| 1 | — | — | $1.6 \times 10^3$ | 100.0 |
|  | ($2'$-$5'$)(A)5 | 10 | $1.5 \times 10^3$ | 93.7 |
|  | ($2'$-$5'$)(A)$_4$PGro | 10 | $2.5 \times 10^1$ | 1.5 |
| 2 | — | — | $1.6 \times 10^4$ | 100.0 |
|  | ($2'$-$5'$)(A)$_4$PGro | 10 | $1.7 \times 10^2$ | 1.1 |
|  | ($2'$-$5'$)(A)$_4$PGro | 1.0 | $2.5 \times 10^3$ | 15.6 |
|  | ($2'$-$5'$)(A)$_4$PGro | 0.1 | $2.1 \times 10^4$ | 131 |

The tests whose results have been collected in Table 1 were carried out as follows.

HeLa cells which grew on glass fragments were micro-injected with 0.5 nl with each of the ($2'$-$5'$)(A)5 or products relating to the concentrations indicated.

One hour later, the cells were infested with vesicular stomative virus (infection multiplicity = 10) and the yield of the virus was determined 18 hours after, by testing of plates in L929 cells.

Considering that 0.5 nl represents a approximately 1/10th of the cell volume, it could be estimated that the final intracytoplasmic concentrations of the oligomers was about 1/10th of the values in Table 1.

As shown by Table 1, unmodified (2'-5')(A)₅ does not effect the production of vesicular stomatitus virus when it is micro-injected into the HeLa cells at an intercytoplasmic concentration of about 1 μm.

On the contrary, the (2'-5')(A)₄PGro reduced the growth of the virus about 100 fold at the same concentration and was still active at the final concentration of 100 nM. Conclusion The chemical modifications introduced into the 2'-5' oligoadenylates, according to the invention, resulted in derivatives which were always active with respect to endoribonuclease and which were stable with respect to the degradation of the phosphodiesterase in acellular extracts, and had an increased antiviral biological activity in the cells.

EXAMPLE 2

Synthesis of γS-(2'-5')(A)ₙOx Red

It is recalled that by γS-(2'-5')(A)ₙOx Red are denoted the compounds which can be represented by the following formula:

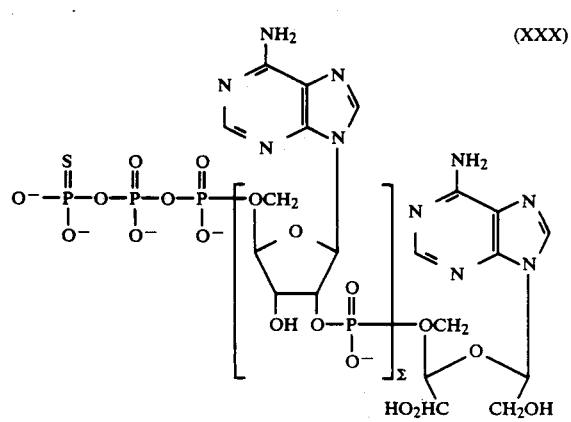

in which Σ is a whole number equal to or greater than 1.

The starting material is adenosine 5'-O-(3-thiotriphosphate) (called below γS ATP) of formula (XXXI):

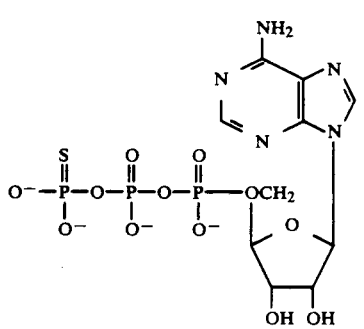

which is polymerised, for example, enzymatically by means of a partly purified preparation of 2-5A, to obtain the compound of formula (XXXII), called below γS-(2'-5')(A)ₙ:

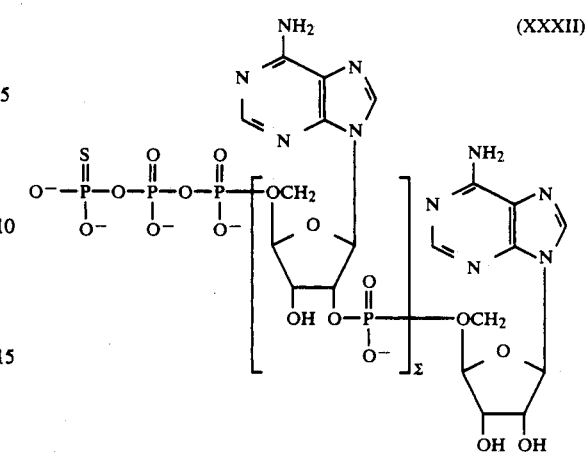

in which Σ is a whole number equal to or greater than 1.

It is then purified, for example, by ion exchange chromatography on DEAE-triacryl. An oxidation is carried out, for example by the periodate ion, of the terminal glycol, to obtain the compound of formula (XXXIII):

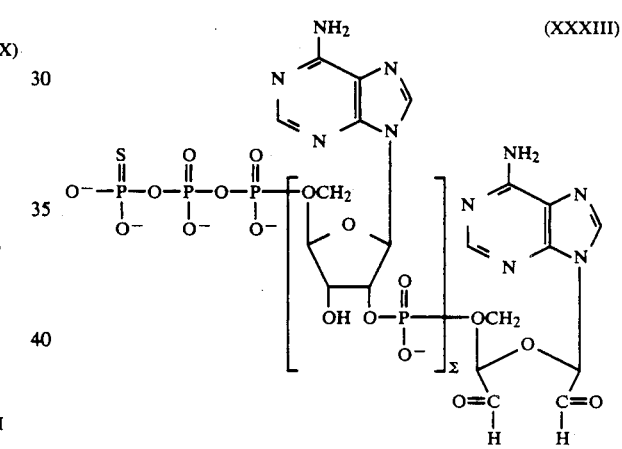

in which Σ is a whole number equal to or greater than 1.

Then the aldehyde groups are reduced, for example by sodium borohydride to obtain γS-(2'-5')(A)ₙOx Red.

Then, for example, by molecular filtration it is purified and analysed by HPLC chromatography.

Metabolic Stability

The oligoadenylates γS(2'-5')(A)ₙ according to the invention and comprising a sulfur atom on the phosphorus group at the gamma position of the triphosphate group linked to the carbon at the 2' position at the first oligonucleoside unit and which can be obtained as indicated above and in particular the S(2'-5')(A) Ox Red have a metabolic stability in an acellular system higher than that of derivatives protected only at their 3'OH ends.

Figure 2:
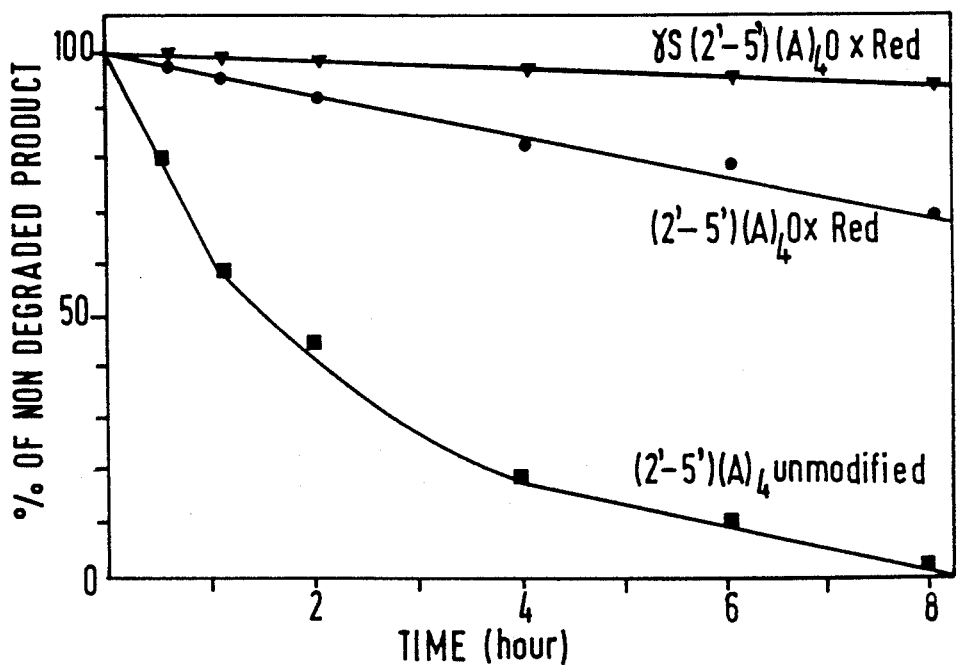
Figure 3:
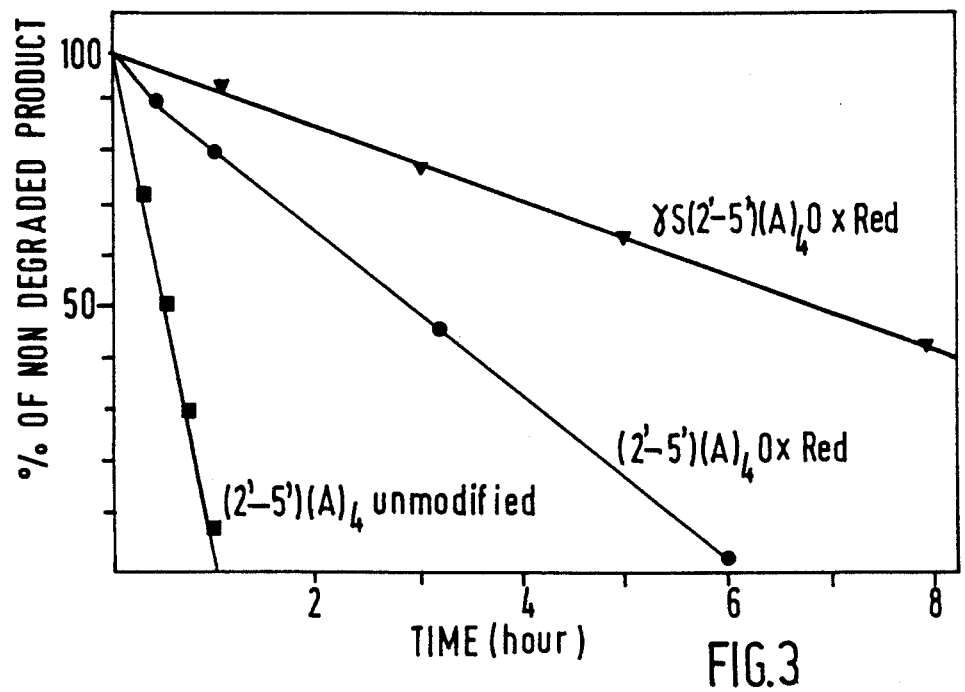

FIGS. 2 and 3 below show the percentages of degradation in an extract of HeLa cells, respectively of unmodified (2'-5')(A)₄, of S-(2'-5')(A)₄Ox Red according to the invention and of (2'-5')(A)₄Ox Red according to the invention.

FIG. 2 relates to a medium containing ATP (1 mM) (very close to the in vivo conditions).

FIG. 3 relates to a medium without ATP.

In each of FIGS. 2 and 3 are shown as abscissae the time (in hours) and in ordinates the percentage of undegraded products.

In FIGS. 2 and 3, the curve marked by triangles relates to $\gamma S(2'-5')(A)_4 Ox$ Red, the curve marked by dots relates to the compound $(2'-5')(A)_4 Ox$ Red and the curve marked by squares relates to the unmodified compound $(2'-5')(A)_4$.

Biological Activity (a) Binding to endoribonuclease

The various analogs according to the invention bind to endoribonuclease with an affinity almost identical to that conventionally used in this field of "radiobinding" described initially by Knight et coll., 1980.

(b) Antiviral activity

The different compounds were micro-injected by means of micropipettes into the cytoplasm of HeLa cells. As shown by the results indicated in Table 2 below, $\gamma S\text{-}(2'-5')(A)_n Ox$ Red exhibits an antiviral activity distinctly greater than that of the unmodified compound $(2'-5')(A)_n$.

TABLE 2

ANTIVIRAL ACTIVITY OF ANALOGS OF $(2'-5')(A)_n$

| DERIVATIVE | CONCEN- TRATION | | TITER OF VIRUS |
|---|---|---|---|
| 1 — | — | | $4.0 \times 10^5$ |
| $(2'-5')(A)_n$ | 10 | μM | $1.2 \times 10^5$ (N.S.) |
| 2 — | — | | $3.3 \times 10^5$ |
| $(2'-5')(A)_n$Ox.Red | 100 | nM | $2.6 \times 10^2$ |
| $(2'-5')(A)_n$Ox.Red | 10 | nm | $5.2 \times 10^3$ |
| 3 — | — | | $3.8 \times 10^5$ |
| $\gamma S(2'-5')(A)_n$ | 10 | μM | $3.3 \times 10^5$ (N.S.) |
| $\gamma S(2'-5')(A)_n$ | 1 | μM | $2.4 \times 10^5$ (N.S.) |
| 4 — | — | | $2.3 \times 10^4$ |
| $\gamma S$ ATP | 10 | μM | $1.3 \times 10^4$ (N.S.) |
| 5 — | — | | $3.8 \times 10^5$ |
| $\gamma S(2'-5')(A)_n$Ox.Red | 1 | μM | <10 |
| $\gamma S(2'-5')(A)_n$Ox.Red | 10 | nM | <10 |
| $\gamma S(2'-5')(A)_n$Ox.Red | 1 | nm | <10 |
| $\gamma S(2'-5')(A)_n$Ox.Red | 10 | pM | $1.1 \times 10^2$ |
| $\gamma S(2'-5')(A)_n$Ox.Red core | 1 | pm | $2.5 \times 10^3$ |
| $\gamma S(2'-5')(A)_n$Ox.Red(1) | 10 | μM | $6.2 \times 10^4$ |

N.S.: Difference with respect to the control not significant
<10: corresponds to totally protected cells
(1): the same product dephosphorylated by alkaline phosphatase The tests, to determine the antiviral activity, were carried out as follows.

HeLa cells (about 200 per experimental spot) attached to a glass support were each micro-injected with $5 \times 10^{-10}$ ml of $(2'-5')(A)_n$ or an analog of $(2'-5')(A)_n$ at the concentrations indicated.

The cells were infected one hour later with the virus of vesicular stomatitis (infection multiplicity = 10) and the viral multiplication was determined 18 hours later by a lysis areas test on L929 mouse fibroblasts. Since $5 \times 10^{-10}$ ml represents about 1/10th of the cellular volume, the final intracellular concentrations in 2-5 A were about 1/10th of the values indicated in this table.

The invention also relates to the salts that the above oligonucleotides can form with bases in particular inorganic or organic bases. Among the inorganic salts, are preferred the salts of sodium or potassium. Among the organic salts, the amine, alkylamine and arylamine salts are prefered, in particular those of secondary amines, such as diethylamine, piperazine, or other tertiary amines, such as methylamine, pyridine, methylpiperazine etc. Among all the latter, the physiologically acceptable salts are prefered. The salts may be freeze dried. The compounds according to the invention have biologically interesting properties, in particular properties of the interferon type, and more particularly an antiviral activity.

The compounds according to the invention are capable of inhibiting the synthesis of DNA, in particular the replication in the cells and/or degradation of viral RNA, thus preventing the synthesis of proteins, more particularly viral proteins in cells infected with the virus at nanomolar concentrations.

The compounds according to the invention are stable and resist degradation by phosphodiesterases and the time of resistance with respect to phosphatases is increased.

A prefered class of compounds according to the invention resist degradation by phosphatases.

The oligonucleotides according to the invention are hence suitable substitutes for interferon and its known applications. They may be prepared reproducibly in highly purified form, as biological reagents, in particular as a comparison reference in qualitative and in quantitative tests, in cell cultures, of compounds of interferon or other substances similar to interferon.

The invention relates also to the pharmaceutically acceptable salts of the oligonucleotides defined above in particular those suitable for in vivo administration.

The invention relates also to pharmaceutical compositions associating the above-said oligonucleotides, preferably in the form of pharmaceutically acceptable salts, with a pharmaceutical vehicle.

The invention thus provides pharmaceutical compositions having an activity similar to that of interferon by using a predetermined chemical compound in the form of high purity, not having toxicity, being stable and easy to manipulate.

The composition according to the invention may be in the form of preparations administrable orally or rectally, by using suitable solids or liquids for such a type of administration or in the form of sterile injectable preparations containing any one at least of the nucleotides in association with suitable sterile liquid vehicles, preferably isotonic.

Other suitable forms of preparations consisting of pommades in which the oligonucleotides of the invention are associated with vehicles in a pommade.

Any one of the conventionally used techniques of preparation for associating interferon with pharmaceutical supports may be used to prepare the pharmaceutical compositions according to the invention.

The oligonucleotides according to the invention may be associated with other suitable vectors, such as liposomes.

The compositions of the invention have antiviral properties and are in particular capable of inhibiting viral diseases which can be followed by tumoral disorders, for example diseases induced by hepatitis B virus or the various forms of virus of herpes.

More generally, the compositions of the invention are useful for the treatment and the prevention of viral diseases, and for antitumoral treatments with respect to tumors capable of being also controlled by treatments with interferon.

It will be noted that the doses at which the compositions are used are determined according to the nature of the disease which afflicts the patient and the particular conditions of health.

Suitable dosages are determined by the physician, as practice may require in these fields of use.

We claim:

1. An oligonucleotide of the formula

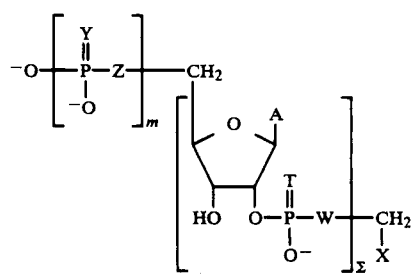

in which Y and T are identical or different and are O, S, Se or NH, Z and W are identical or different and are O, S or NH, at least one of the substituents Y and Z in at least one of the phosphate moieties being different from oxygen, X is selected from the group consisting of

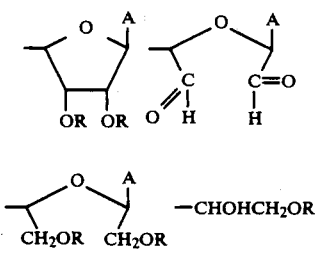

R is H or

$R_1$ is alkyl of 1 to 5 carbon atoms or phenyl,
$\Sigma$ is a whole number equal to
  n when X is —CHOHCH$_2$OR, or
  n−1 when X is

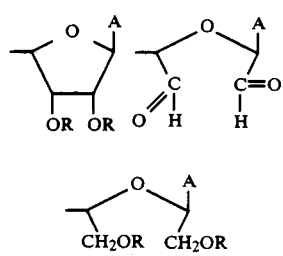

wherein n is an integer of 2 to 10, m is an integer of 1 to 3, and A is adenine or a derivative selected from the group consisting of

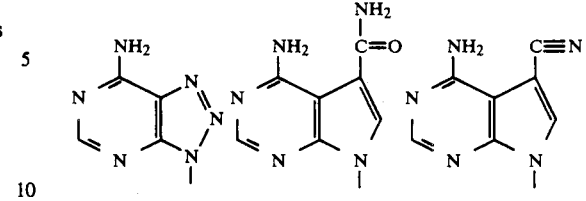

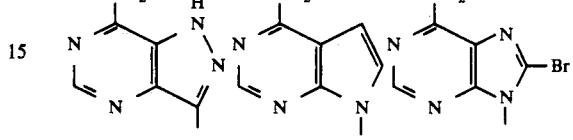

and the physiologically acceptable salts thereof.

2. The oligonucleotide of claim 1, having the formula

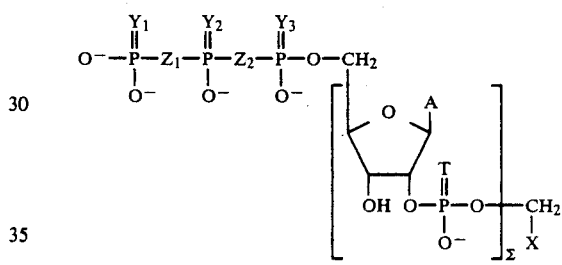

in which $Y_1$, $Y_2$, $Y_3$ and T are identical or different and are O, S, Se or NH and $Z_1$ and $Z_2$ are identical or different and are, O, S or NH, at least one of the substituents $Y_1$, $Y_2$, $Y_3$, $Z_1$ and $Z_2$ being different from oxygen.

3. The oligonucleotides of claim 1, having the formula

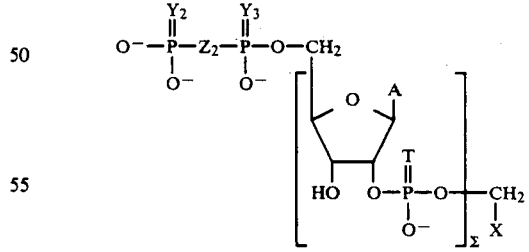

in which $Y_2$, $Y_3$ and T are identical or different and are O, S, Se or NH, $Z_2$ is O, S or NH, at least one of the substituents $Y_2$, $Y_3$ and $Z_2$ being different from oxygen, R is hydrogen, and n is an integer between 2 to 10, inclusive.

4. The oligonucleotide of claim 1, having the formula

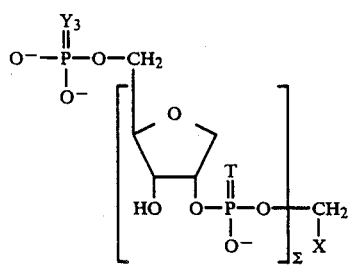

in which $Y_3$ is S, Se or NH, T is O, S, Se or NH, R is hydrogen, and n is an integer between 2 and 10, inclusive.

5. The oligonucleotide of claim 1 in which T is oxygen.

6. The oligonucleotide of claim 2 in which T is oxygen.

7. The oligonucleotide of claim 3 in which T is oxygen.

8. The oligonucleotide of claim 4 in which T is oxygen.

9. The oligonucleotide of claim 1, wherein X is selected from the group consisting of

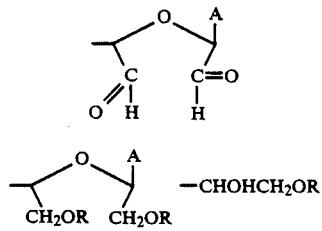

10. The oligonucleotide of claim 9, wherein Z and W are oxygen.

11. The oligonucleotide of claim 10, selected from the group consisting of oligonucleotides of the formulas

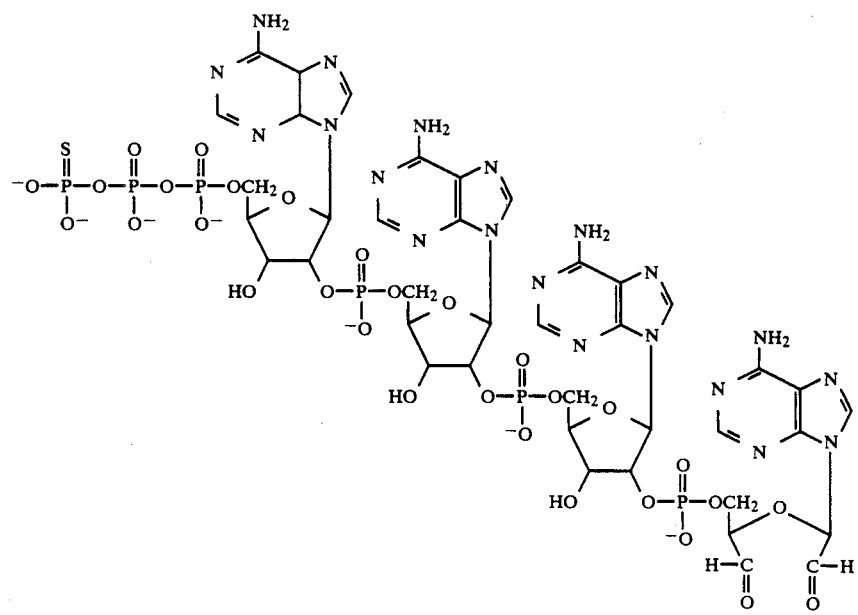

-continued
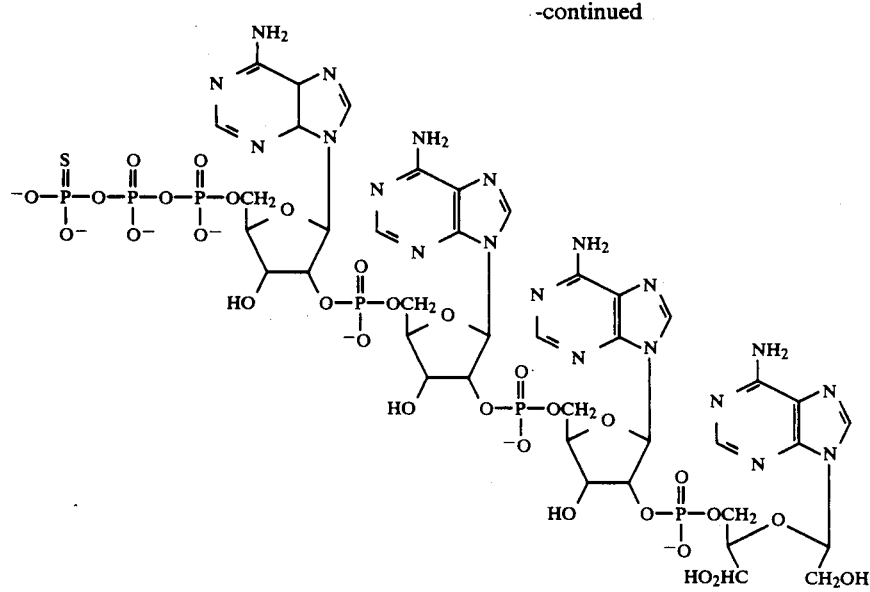
and
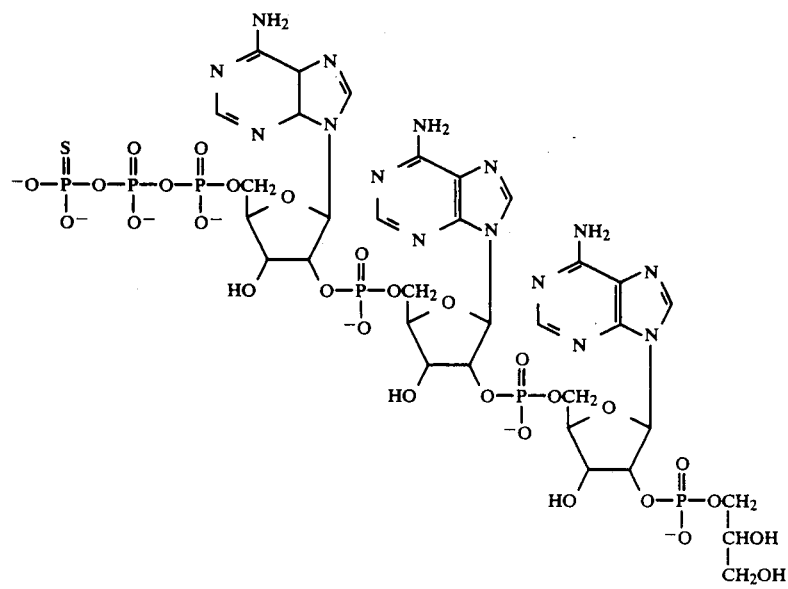
12. A pharmaceutical composition comprising the oligonucleotide of claim 9 and a pharmaceutically acceptable carrier.
13. A pharmaceutical composition comprising an oligonucleotide of claim 11 and a pharmaceutically acceptable carrier.
* * * * *